United States Patent
Farr et al.

(10) Patent No.: US 9,033,870 B2
(45) Date of Patent: May 19, 2015

(54) PLUGGABLE VISION MODULE AND PORTABLE DISPLAY FOR ENDOSCOPY

(75) Inventors: Mina Farr, Palo Alto, CA (US); Franklin J. Wall, Jr., Vacaville, CA (US); Chris Togami, San Jose, CA (US); Gary D. Sasser, San Jose, CA (US)

(73) Assignee: VIVID MEDICAL, INC., Palo Alto, CA (US)

( * ) Notice: Subject to any disclaimer, the term of this patent is extended or adjusted under 35 U.S.C. 154(b) by 636 days.

(21) Appl. No.: 12/413,457

(22) Filed: Mar. 27, 2009

(65) Prior Publication Data

US 2009/0318758 A1 Dec. 24, 2009

Related U.S. Application Data

(63) Continuation-in-part of application No. 12/111,107, filed on Apr. 28, 2008, now Pat. No. 8,602,971, which is a continuation-in-part of application No. 11/233,684, filed on Sep. 23, 2005, now Pat. No. 8,480,566.

(Continued)

(51) Int. Cl.
 *A61B 1/06* (2006.01)
 *A61B 1/00* (2006.01)
 (Continued)

(52) U.S. Cl.
 CPC .............. *A61B 1/0676* (2013.01); *A61B 1/005* (2013.01); *A61B 1/00098* (2013.01); *A61B 1/018* (2013.01);
 (Continued)

(58) Field of Classification Search
 USPC ......... 600/109, 104, 160, 175, 128, 172, 176, 600/139
 See application file for complete search history.

(56) References Cited

U.S. PATENT DOCUMENTS

| | | |
|---|---|---|
| 4,000,417 A | 12/1976 | Adkisson et al. |
| 4,337,761 A | 7/1982 | Upsher |

(Continued)

FOREIGN PATENT DOCUMENTS

| | | |
|---|---|---|
| CN | 1452472 A | 10/2003 |
| CN | 1794944 A | 6/2006 |

(Continued)

OTHER PUBLICATIONS

International Search Report and Written Opinion dated Oct. 30, 2009 as issued in International Application No. PCT/US2009/041118 filed Apr. 20, 2009.

(Continued)

*Primary Examiner* — Anhtuan T Nguyen
*Assistant Examiner* — William Chou
(74) *Attorney, Agent, or Firm* — Maschoff Brennan

(57) ABSTRACT

Various embodiments for providing removable and pluggable opto-electronic modules for illumination and imaging for endoscopy or borescopy are provided for use with portable display devices. Generally, various medical or industrial devices can include one or more solid state or other compact electro-optic illuminating elements located thereon. Additionally, such opto-electronic modules may include illuminating optics, imaging optics, and/or image capture devices. The illuminating elements may have different wavelengths and can be time-synchronized with an image sensor to illuminate an object for imaging or detecting purpose or other conditioning purpose. The removable opto-electronic modules may be plugged in on the exterior surface of a device, inside the device, deployably coupled to the distal end of the device, or otherwise disposed on the device.

25 Claims, 21 Drawing Sheets

Related U.S. Application Data

(60) Provisional application No. 60/612,889, filed on Sep. 24, 2004, provisional application No. 61/082,432, filed on Jul. 21, 2008.

(51) Int. Cl.
  *A61B 1/04* (2006.01)
  *A61B 1/018* (2006.01)
  *A61B 17/34* (2006.01)
  *A61B 19/00* (2006.01)
  A61B 1/005 (2006.01)
  A61B 1/05 (2006.01)
  A61B 17/00 (2006.01)

(52) U.S. Cl.
  CPC ............ *A61B 1/05* (2013.01); *A61B 1/0638* (2013.01); *A61B 1/0684* (2013.01); *A61B 17/00234* (2013.01); *A61B 17/3421* (2013.01); *A61B 17/3439* (2013.01); *A61B 19/5225* (2013.01); *A61B 2017/3484* (2013.01); *A61B 2019/261* (2013.01); *A61B 2019/4868* (2013.01); *A61B 2019/521* (2013.01); *A61B 2019/5229* (2013.01); *A61B 1/043* (2013.01)

(56) References Cited

U.S. PATENT DOCUMENTS

| | | | |
|---|---|---|---|
| 4,437,458 A | 3/1984 | Upsher | |
| 4,473,841 A | 9/1984 | Murakoshi et al. | |
| 4,527,553 A | 7/1985 | Upsher | |
| 4,869,238 A | 9/1989 | Opie et al. | |
| 4,901,708 A | 2/1990 | Lee | |
| 4,974,076 A | 11/1990 | Nakamura et al. | |
| 4,982,729 A | 1/1991 | Wu | |
| 5,025,778 A * | 6/1991 | Silverstein et al. | 600/104 |
| 5,056,163 A | 10/1991 | Chou | |
| 5,062,697 A | 11/1991 | Mitchell | |
| 5,166,787 A * | 11/1992 | Irion | 348/75 |
| 5,203,320 A | 4/1993 | Augustine | |
| 5,261,392 A | 11/1993 | Wu | |
| 5,285,397 A | 2/1994 | Heier et al. | |
| 5,305,121 A | 4/1994 | Moll | |
| 5,381,784 A | 1/1995 | Adair | |
| 5,475,316 A | 12/1995 | Hurley et al. | |
| 5,494,483 A | 2/1996 | Adair | |
| 5,538,497 A * | 7/1996 | Hori | 600/182 |
| 5,614,941 A | 3/1997 | Hines | |
| 5,643,221 A | 7/1997 | Bullard | |
| 5,645,519 A | 7/1997 | Lee et al. | |
| 5,647,840 A | 7/1997 | D'Amelio et al. | |
| 5,653,677 A | 8/1997 | Okada et al. | |
| 5,667,473 A * | 9/1997 | Finn et al. | 600/104 |
| 5,749,830 A | 5/1998 | Kaneko et al. | |
| 5,800,342 A | 9/1998 | Lee et al. | |
| 5,836,867 A * | 11/1998 | Speier et al. | 600/112 |
| 5,840,013 A | 11/1998 | Lee et al. | |
| 5,895,350 A | 4/1999 | Hori | |
| 5,908,294 A | 6/1999 | Schick et al. | |
| 6,066,090 A | 5/2000 | Yoon | |
| 6,106,457 A | 8/2000 | Perkins et al. | |
| 6,178,346 B1 | 1/2001 | Amundson et al. | |
| 6,203,493 B1 | 3/2001 | Ben Haim | |
| 6,277,064 B1 | 8/2001 | Yoon | |
| 6,352,517 B1 | 3/2002 | Flock et al. | |
| 6,441,958 B1 | 8/2002 | Yeung et al. | |
| 6,461,359 B1 | 10/2002 | Tribus et al. | |
| 6,471,643 B1 | 10/2002 | Henderson | |
| 6,485,413 B1 | 11/2002 | Boppart et al. | |
| 6,525,875 B1 | 2/2003 | Lauer | |
| 6,616,603 B1 | 9/2003 | Fontana | |
| 6,648,816 B2 | 11/2003 | Irion et al. | |
| 6,711,283 B1 | 3/2004 | Soenksen | |
| 6,736,773 B2 | 5/2004 | Wendlandt et al. | |
| 6,762,794 B1 | 7/2004 | Ogino | |
| 6,878,109 B2 | 4/2005 | Yamaki et al. | |
| 6,916,286 B2 | 7/2005 | Kazakevich | |
| 6,986,738 B2 * | 1/2006 | Glukhovsky et al. | 600/109 |
| 7,029,435 B2 * | 4/2006 | Nakao | 600/153 |
| 7,048,685 B2 | 5/2006 | Sakiyama | |
| 7,074,182 B2 | 7/2006 | Rovegno | |
| 7,413,543 B2 * | 8/2008 | Banik et al. | 600/129 |
| 7,435,218 B2 | 10/2008 | Krattiger et al. | |
| 7,442,166 B2 | 10/2008 | Huang et al. | |
| 7,591,783 B2 | 9/2009 | Boulais et al. | |
| 7,819,877 B2 | 10/2010 | Guzman et al. | |
| 7,892,169 B2 | 2/2011 | Gono et al. | |
| 7,951,072 B2 * | 5/2011 | Adams et al. | 600/121 |
| 7,955,255 B2 | 6/2011 | Boulais et al. | |
| 8,212,858 B2 | 7/2012 | Schechterman et al. | |
| 2001/0007051 A1 | 7/2001 | Nakashima | |
| 2002/0001202 A1 | 1/2002 | Williams et al. | |
| 2002/0120181 A1 | 8/2002 | Irion | |
| 2002/0135871 A1 | 9/2002 | Vodyanoy et al. | |
| 2002/0143239 A1 | 10/2002 | Henzler | |
| 2002/0161283 A1 | 10/2002 | Sendai | |
| 2003/0023150 A1 | 1/2003 | Yokoi et al. | |
| 2003/0120130 A1 | 6/2003 | Glukhovsky et al. | |
| 2004/0039242 A1 | 2/2004 | Tolkoff et al. | |
| 2004/0147806 A1 | 7/2004 | Adler | |
| 2004/0196364 A1 | 10/2004 | Takahashi | |
| 2004/0204628 A1 | 10/2004 | Rovegno | |
| 2005/0001899 A1 | 1/2005 | Banju et al. | |
| 2005/0014994 A1 | 1/2005 | Fowler et al. | |
| 2005/0024505 A1 | 2/2005 | Kawachi | |
| 2005/0038321 A1 | 2/2005 | Fujita et al. | |
| 2005/0043586 A1 | 2/2005 | Suzushima | |
| 2005/0043588 A1 | 2/2005 | Tsai | |
| 2005/0059860 A1 | 3/2005 | Matsumoto et al. | |
| 2005/0085691 A1 * | 4/2005 | Nakao | 600/128 |
| 2005/0096502 A1 | 5/2005 | Khalili | |
| 2005/0154262 A1 | 7/2005 | Banik et al. | |
| 2005/0180700 A1 | 8/2005 | Farr | |
| 2005/0182297 A1 | 8/2005 | Gravenstein | |
| 2005/0222499 A1 | 10/2005 | Banik et al. | |
| 2005/0234296 A1 | 10/2005 | Saadat et al. | |
| 2005/0237605 A1 | 10/2005 | Vodyanoy et al. | |
| 2005/0240077 A1 | 10/2005 | Rovegno | |
| 2005/0272975 A1 | 12/2005 | McWeeney et al. | |
| 2006/0018017 A1 | 1/2006 | Takahashi | |
| 2006/0020171 A1 | 1/2006 | Gilreath | |
| 2006/0041193 A1 | 2/2006 | Wright et al. | |
| 2006/0069313 A1 | 3/2006 | Couvillon et al. | |
| 2006/0069314 A1 | 3/2006 | Farr | |
| 2006/0167531 A1 | 7/2006 | Gertner et al. | |
| 2006/0178556 A1 | 8/2006 | Hasser et al. | |
| 2006/0189845 A1 | 8/2006 | Maahs et al. | |
| 2006/0287582 A1 | 12/2006 | Toda | |
| 2007/0015964 A1 | 1/2007 | Eversull et al. | |
| 2007/0058249 A1 | 3/2007 | Hirose et al. | |
| 2007/0073109 A1 | 3/2007 | Irion | |
| 2007/0106117 A1 | 5/2007 | Yokota | |
| 2007/0106121 A1 | 5/2007 | Yokota et al. | |
| 2007/0106122 A1 | 5/2007 | Yokota et al. | |
| 2007/0167702 A1 | 7/2007 | Hasser et al. | |
| 2007/0213590 A1 * | 9/2007 | Squicciarini | 600/172 |
| 2007/0225561 A1 | 9/2007 | Watanabe et al. | |
| 2007/0276183 A1 | 11/2007 | Melder | |
| 2007/0292939 A1 | 12/2007 | Chen | |
| 2008/0045800 A2 | 2/2008 | Farr | |
| 2008/0051632 A1 | 2/2008 | Ito et al. | |
| 2008/0207996 A1 | 8/2008 | Tsai | |
| 2008/0208006 A1 | 8/2008 | Farr | |
| 2009/0099550 A1 * | 4/2009 | Carrillo et al. | 604/528 |
| 2010/0022831 A1 | 1/2010 | Zifeng et al. | |
| 2010/0198009 A1 | 8/2010 | Farr et al. | |
| 2010/0234925 A1 | 9/2010 | Harris et al. | |
| 2010/0312059 A1 | 12/2010 | Mcgrath | |

FOREIGN PATENT DOCUMENTS

| | | |
|---|---|---|
| CN | 101634749 A | 1/2010 |
| JP | H05285154 A | 11/1993 |
| JP | H05337073 A | 12/1993 |

(56) References Cited

FOREIGN PATENT DOCUMENTS

| JP | 11216113 A | 8/1999 |
|---|---|---|
| JP | 2000245689 A | 9/2000 |
| JP | 2003093399 A | 4/2003 |
| JP | 2003-220023 A | 8/2003 |
| JP | 2003334157 A | 11/2003 |
| KR | 10-2008-0089579 A | 10/2008 |
| WO | 0211608 A2 | 2/2002 |
| WO | 2004086957 A2 | 10/2004 |

OTHER PUBLICATIONS

PCT/US2009/041118, Apr. 20, 2009, Farr et al.
U.S. Appl. No. 12/759,169, filed Apr. 13, 2010, Farr et al.
U.S. Appl. No. 12/771,087, filed Apr. 30, 2010, Farr et al.
U.S. Appl. No. 11/233,684, Jul. 13, 2009, Restriction Requirement.
U.S. Appl. No. 11/233,684, Nov. 12, 2009, Office Action.
U.S. Appl. No. 11/233,684, May 14, 2010, Office Action.
International Search Report dated Apr. 23, 2012 as received in application No. PCT/US2011/052039.
Written Opinion of the International Searching Authority dated Apr. 23, 2012 as received in application No. PCT/US2011/052039.
KR Office Action dated Jul. 30, 2014 as received in Application No. 10-2013-7009566 (English Translation).
Chinese Office Action dated Dec. 3, 2014 as received in Application No. 201180049790.7 (English Translation).

\* cited by examiner

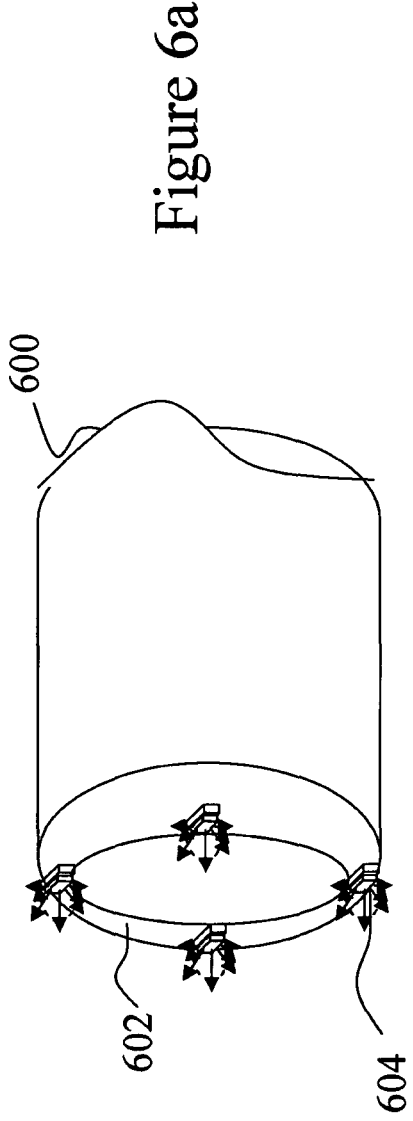
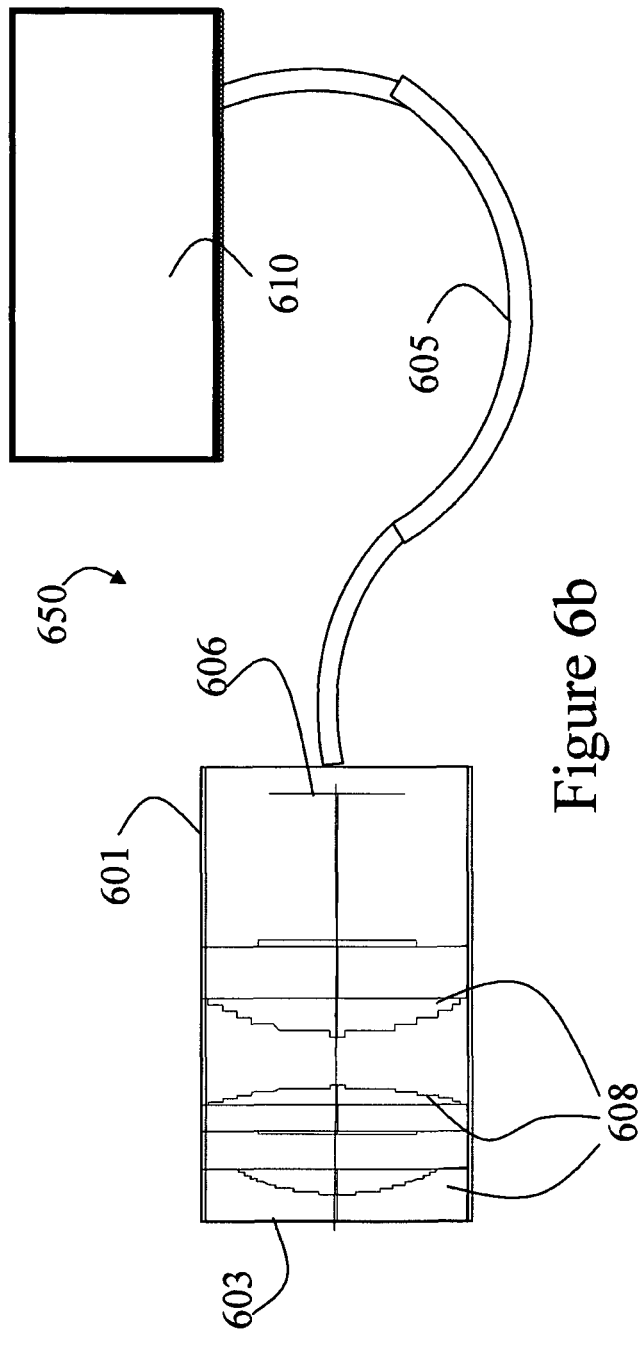
Figure 6a
Figure 6b

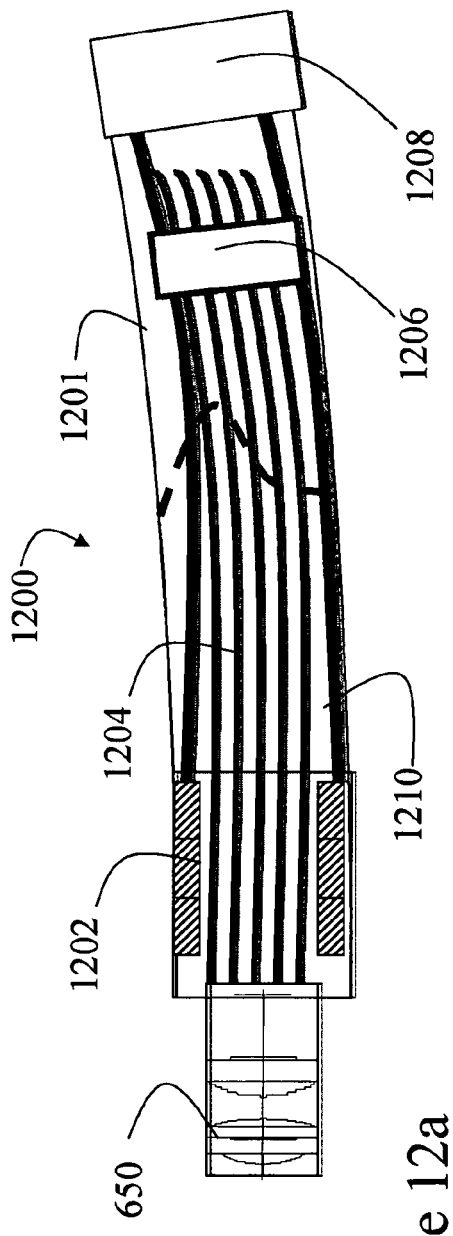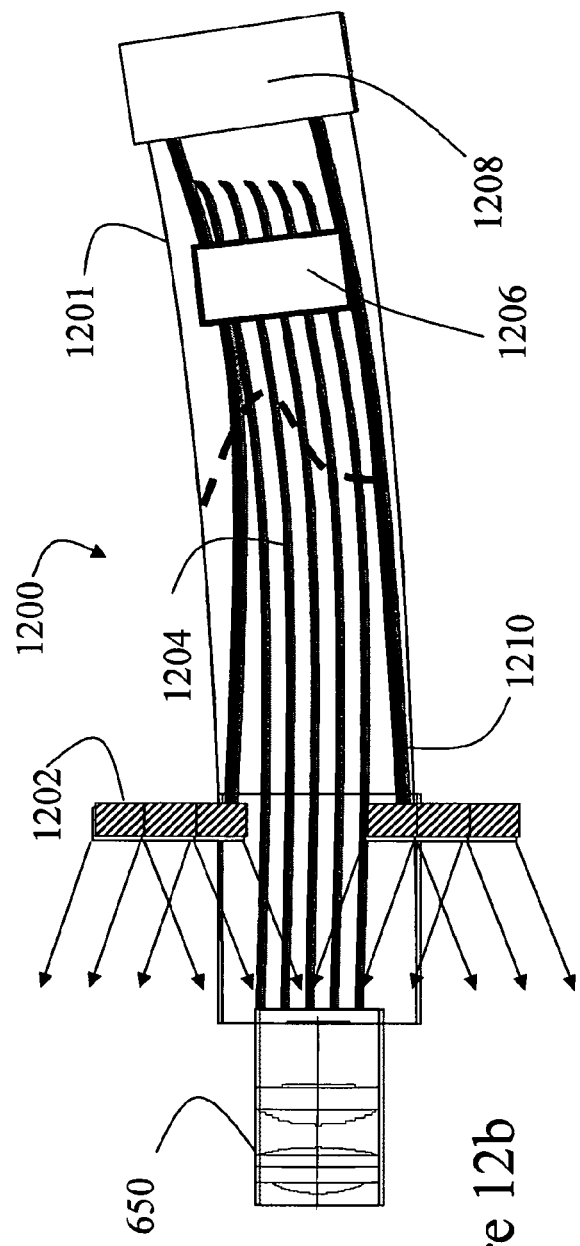
Figure 12a
Figure 12b

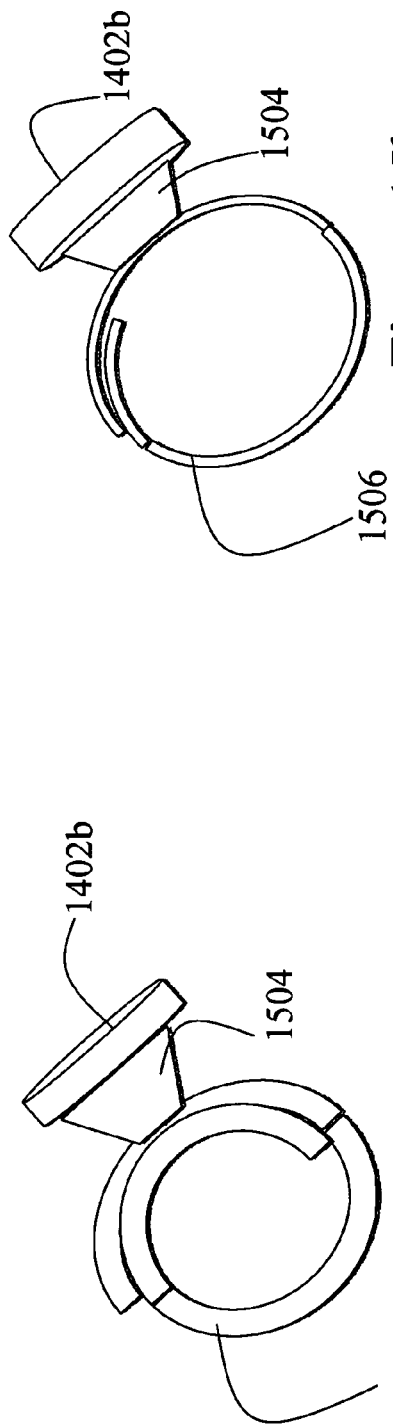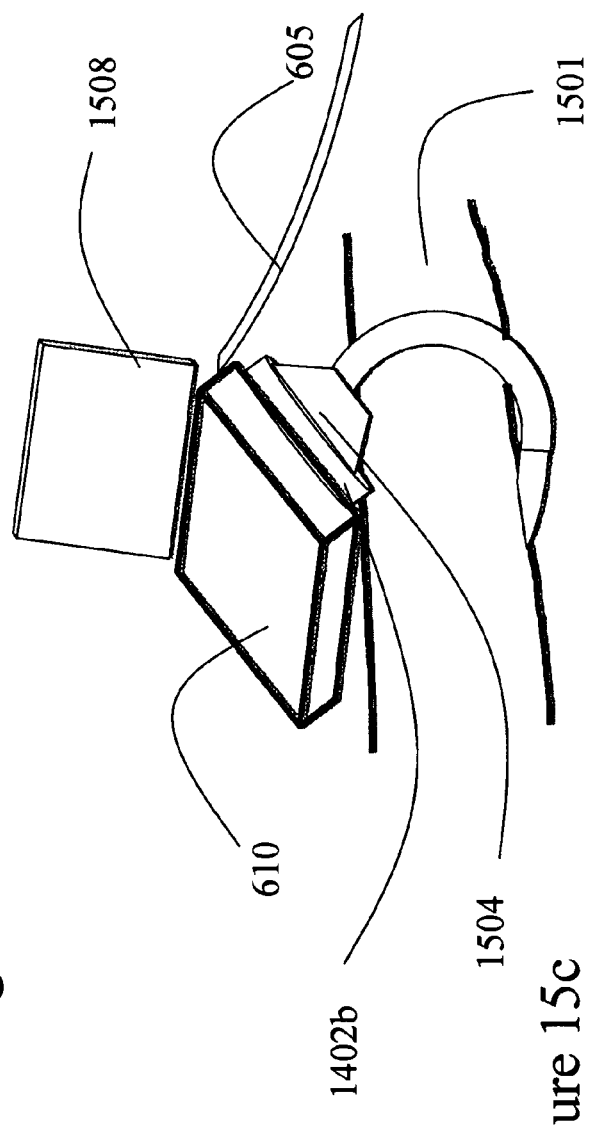
Figure 15a
Figure 15b
Figure 15c

PLUGGABLE VISION MODULE AND PORTABLE DISPLAY FOR ENDOSCOPY

CROSS-REFERENCE TO RELATED APPLICATIONS

This patent application:

(i) is a continuation-in-part of U.S. patent application Ser. No. 12/111,107, filed Apr. 28, 2008 and entitled OPTO-ELECTRONIC ILLUMINATION AND VISION MODULE FOR ENDOSCOPY, which is a continuation-in-part of U.S. patent application Ser. No. 11/233,684, filed Sep. 23, 2005 and entitled SOLID STATE ILLUMINATION FOR ENDOSCOPY, which claims the benefit of U.S. Provisional Patent Application Ser. No. 60/612,889, filed Sep. 24, 2004 and entitled SOLID STATE ILLUMINATION FOR ENDOSCOPY; and (ii) claims the benefit of and priority to U.S. Provisional Patent Application Ser. No. 61/082,432, filed Jul. 21, 2008 and entitled INDIVIDUAL STEREO VIEWER.

The above-identified patent applications are hereby incorporated herein by reference in their entirety.

BACKGROUND OF THE INVENTION

1. The Field of the Invention

The present invention relates generally to apparatus for visualization of endoscopic and borescopic fields, in minimally invasive surgical (MIS) procedures, general or diagnostic medical or industrial procedures using endoscopes or borescopes, respectively. More particularly, embodiments of the invention relate to use of pluggable and removable vision systems in endoscopic and borescopic procedures, as a means of image capture.

2. The Relevant Technology

Endoscopy is used in both diagnostic and surgical procedures. Currently, MIS procedures, as opposed to open surgical procedures, are routinely done in almost all hospitals. Minimally invasive techniques minimize trauma to the patient by eliminating the need to make large incisions. This both reduces the risk of infection and reduces the patient's hospital stay. Endoscopic procedures in MIS use different types of endoscopes as imaging means, giving the surgeon an inside-the-body view of the surgical site. Specialized endoscopes are named depending on where they are intended to look. Examples include: cystoscope (bladder), nephroscope (kidney), bronchoscope (bronchi), laryngoscope (larynx+the voice box), otoscope (ear), arthroscope (joint), laparoscope (abdomen), gastrointestinal endoscopes, and specialized stereo endoscopes used as laparoscopes or for endoscopic cardiac surgery.

The endoscope may be inserted through a tiny surgical incision to view joints or organs in the chest or abdominal cavity. More often, the endoscope is inserted into a natural body orifice such as the nose, mouth, anus, bladder or vagina. There are three basic types of endoscopes: rigid, semi-rigid, and flexible. The rigid endoscope comes in a variety of diameters and lengths depending on the requirements of the procedure. Typical endoscopic procedures require a large amount of equipment. The main equipment used in conjunction to the visual part of the endoscopic surgery are the endoscope body, fiber optics illumination bundles, illumination light source, light source controller, imaging camera, camera control module, and video display unit.

The laparoscope is a rigid endoscope as illustrated in FIG. 1. It allows for visualization of the abdominopelvic cavities for diagnostic or surgical techniques. The laparoscope is inserted into the peritoneal cavity via a cannula that runs through the abdominal wall. There are many different features of laparoscopes, such as the size and field of vision, which determine the effectiveness of the instrument.

As illustrated in FIG. 1, the basic laparoscope is made up of a long thin tube 101 with an eyepiece 103 at one end for viewing into the patient. Fiber optic light introduced to the endoscope at fiber port 102, and launched into fiber optics 302 (FIG. 3), passes through the endoscope body 101, illuminating the area 304 that is being observed, as illustrated by radiation pattern 306 in FIG. 3. Laparoscopes are characterized by diameter and the direction of view. The direction of view is the angle 107 between the axis 105 of the laparoscope and the center field of view 106, as illustrated in FIG. 1. Typical endoscopes have lengths of approximately 30 cm and diameters in the range of 4 to 10 mm. Laparoscopes consist of two important lenses, the ocular lens at the eyepiece and the objective lens 308 at the distal end of the endoscope 300 in FIG. 3. Other lens sets acting as relay lenses 310 in FIG. 3, are used in-between the objective lens and the eye piece or the CCD camera or image position 312. Imaging rays 314 traverse the length of the scope through all the imaging optics.

The rigid endoscope also comes in different viewing angles: 120 degree or retrograde, for viewing backward; 90 degree and 70 degree for lateral viewing; 30 degree (104 as illustrated in FIG. 1) and 45 degree for forward oblique views; and 0 degree for forward viewing. The angle of the objective lens 308 used is determined by the position of the structure to be viewed.

Other surgical instruments and tools are also inserted into the body, for the operation and specific surgical manipulation by the surgeon. The insertion is done through open tubes provided inside the endoscope body for instrument insertion, such as in gastrointestinal endoscopes, or through separate incisions in the abdominal or chest wall 202, as illustrated in FIG. 2, using cannula 200 (straight or curved stainless steel or plastic tubes which are inserted into a small opening or incision in the skin). The cannula opening at the proximal end 204 outside the body is used to guide different instruments inside the body, where they are exposed to the inside of body at the distal end 206 of the cannula. Cannulas can make a seal at the incision site 208.

In a typical gastrointestinal endoscope, a tool opening is provided at the distal end of the scope, where inserted medical instruments gain access to the body following the scope body.

Endoscopes can be diagnostic, for observation only, or operative, having channels or ports for irrigation, suction, and the insertion of accessory instruments when a surgical procedure is planned. Thus, endoscope bodies also could provide mechanical or electrical control sections, buttons for valves such as a suction valve, a CO2 valve, a water bottle connector, a water feed, a suction port, etc. The common component that all endoscopes must be equipped with is a light guide section for illumination.

An illustration showing typical endoscope optics is shown in FIG. 3. Common imaging sections of the endoscope are an ocular or eyepiece, relay lenses 310 (in the case of rigid scopes), a flexible imaging fiber-optic bundle (in the case of flexible scopes), and an objective lens system 308. Endoscopes are either used as stand alone units, with the surgeon looking into the scope from the ocular or eye piece of the endoscope, or in conjunction with digital cameras, where an image of the surgical site is incident on the image capture device (charge coupled device or CCD) of the camera. Using a display device, the surgeon performs the operation looking at the image on the video monitor.

With recent technology improvements in the field of electronic imaging reducing the size of the image capture device (e.g., CCD), some endoscopes used in MIS and diagnostic procedures are equipped with a high resolution distal end camera system, commonly referred to as Chip on a Stick, one example of which is illustrated in FIG. 4 as camera system 400. These flexible endoscopes use a CCD chip 402 at the distal end of the endoscope directly capturing the image through the objective lens 404, in which case the flexible part 406 of the endoscope body contains only power and communication wires for the CCD camera at the distal tip, rather than imaging optics 408 located in a rigid portion 404 of the endoscope. Light guides 410 running the length of the endoscope are still necessary for this type of electronic scope to provide adequate lighting 412 of the surgical site 414 for imaging purposes.

Other, more complicated MIS systems make use of robotic and articulating surgical tools and instruments, and/or provide stereoscopic images of the surgical site for the surgeon, improving the surgeon's dexterity, precision and speed of operation. In these more sophisticated MIS imaging applications more specific types of illumination systems or multiple illuminators are used.

Color CCD cameras use alternate color dies on the individual CCD pixels, to capture color images. Green and red, and green and blue pixels are alternated in rows. This spatial color sampling limits the color resolution of the color CCD cameras, since each pixel is dedicated to capturing a single color in the color image.

3 chip CCD cameras (red CCD chip, blue CCD chip, and green CCD chip) are also used in high resolution applications, where all the pixels in each CCD are dedicated to detecting the single color content of the image. The individual color captured images from the 3 CCDs are then put together electronically, as the multi-color image is reproduced on the viewing display. Three chip CCD cameras are expensive and bulky.

Recent advances in illumination and image capture technology demonstrate the rapid changes that can occur in the capabilities of emerging illumination and imaging systems. For instance, very compact high mega pixel cameras are currently being incorporated widely in cellular phone cameras, whereas just a few years ago this was not possible. It is quite likely that other technological advances in imaging and illumination will occur that can be used in endoscopic medical devices. And, although it may be desirable to incorporate the latest technological advances in illumination and imaging into an endoscopic medical device, this is often impossible without designing and purchasing a brand new replacement of the complete medical device having the improved technology. This complete new solution, however, can be prohibitively expensive especially in the circumstances that the medical providers are under high pressure to reduce cost. Incorporation of the advanced high quality opto-electronics in current and future low cost medical procedures can also be nearly impossible.

Medical diagnostic and treatment procedures are also becoming more available in mobile settings. However, conventional high quality imaging devices are generally not available in convenient packages that are portable and usable without an elaborate setup.

Due to delicate and complicated nature of current endoscope illumination and vision technology, current high performance endoscopes are often limited in sterilization capability, and for the major part not autoclavable. This shortcoming not only limits the life time of these endoscopes to limited number of procedures, but also creates possibility of infection with multiple sterilization and disinfection procedures performed on the current scopes.

BRIEF SUMMARY OF THE INVENTION

These and other limitations are overcome by embodiments of the invention which relate to removable and pluggable illumination and vision systems that can be coupled to the distal end or housed within the body of a single use removable body, and subsequently attached to various medical devices, including various endoscopic devices used as single use disposable unit, or autoclavable medical access devices used in minimally invasive surgical and other diagnostic procedures. Removable and pluggable illumination and vision systems according to some embodiments of the invention include one or more solid state light sources, illumination optics (such as wave guides) and optionally include separate imaging optics and image capture devices, collectively referred to as Opto-Electronic (OE) illumination and vision modules. Removable and pluggable OE illumination and vision modules may additionally include accompanying electronics for process and transfer of the image. Embodiments of the invention also relate to the layouts and functionality of such removable and pluggable vision systems within the body of a disposable endoscope or other disposable medical devices, or within a disposable container in which the removable and pluggable OE illumination and vision modules are housed, and plugged onto a separate non-disposable medical access device or carrier. Embodiments of the invention additionally relate to general layouts of such removable and pluggable vision systems incorporating mechanisms enabling stereoscopic or hyper Field of View (FOV) visual systems.

Embodiments of the invention alternately or additionally include mobile and wearable displays that take advantage of the above embodiments. Some embodiments of mobile and wearable displays can enable minimally invasive surgical and other diagnostic procedures to be performed with minimal setup needs and/or in remote locations.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

To further clarify the above and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 6a illustrates LED illumination at the distal end of a disposable endoscope or cannula body;

FIG. 6b illustrates an OE vision module comprising a miniature camera unit that can be plugged into the distal end of a flexible or rigid medical device and/or connected to a remote portable display and control unit through flexible electrical circuitry;

FIG. 11b illustrates an articulating flexible medical device being inserted into the pluggable OE illumination and vision module of FIG. 11a;

FIGS. 12a and 12b illustrate an example of an LED illumination system that employs side rotational deployment of OE LED illuminators in conjunction with the pluggable OE vision module of FIG. 6b;

FIGS. 14b-14d illustrate various mounting mechanisms that can be employed to adjustably position the portable display of FIG. 14a;

FIGS. 15a-15c illustrate an embodiment of an adjustable, quick mount mechanism for the portable display in FIG. 14a that can be employed to adjustably mount the portable display on a user's arm or wrist;

DETAILED DESCRIPTION OF THE EXEMPLARY EMBODIMENTS

Example embodiments of the invention are directed to removable solid state opto-electronic vision modules, that can include monochromatic, polychromatic visible, Ultra Violet (UV), and/or Infra Red (IR) solid state light sources such as high power Light Emitting Devices (LEDs) and Laser Diodes as a means of illumination and one or more opto-electronic imaging systems for image capture in diagnostic or surgical endoscopic procedures, or functional borescopic systems.

In various endoscope geometries, it is also possible to install and remove the opto-electronic imaging system along with the removable LED illuminator systems or use the current means of illumination, allowing implementation of a removable and pluggable opto-electronic or electro-optic (OE or EO) illumination and/or vision module, as described more fully below. The removability and pluggability of such OE vision modules described herein can provide instantly upgradeable illumination and image capture systems without any necessity to replace an entire medical or other functional device still having a remaining useful life.

Advantageously, with the OE vision module removed from the medical device that houses the pluggable OE vision module, the medical device can be made autoclavable, which is a highly desirable safety feature not currently available to many endoscopes.

In particular, these removable and pluggable OE illumination and vision modules can be incorporated with a protective disposable cover, at the distal end of single use disposable or reusable endoscope, borescope, surgical or industrial tools, or be incorporated inside the distal tip end of single use cannulas, or the body of other disposable medical procedure functional devices. They can also be incorporated in a body that is inserted separately, or in conjunction with a lighted or dark scope, into the body. The OE illumination and vision module schemes of the present invention can replace, or can be used in addition to, conventional fiber optic illumination system and other diagnostic devices such as ultrasound imaging used in endoscopy and borescopy.

Figure 1:
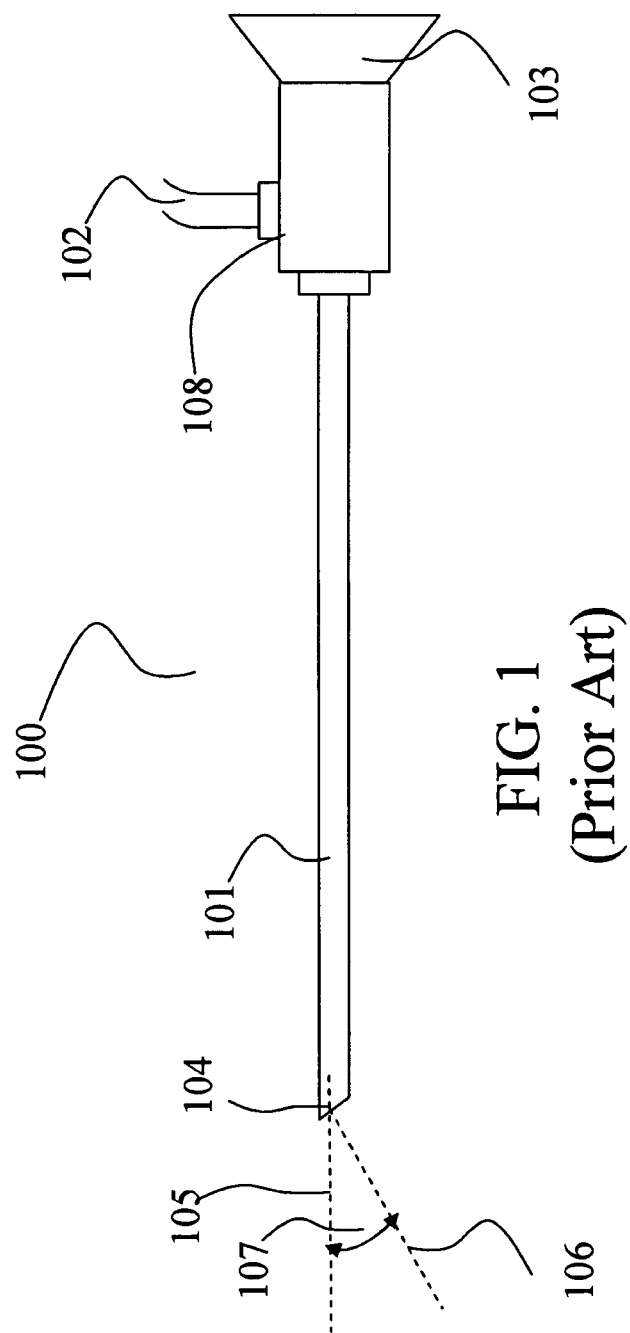
FIG. 1 illustrates a typical angled endoscope, with fiber optic light port for illumination, and an eye piece for viewing.
Figure 2:
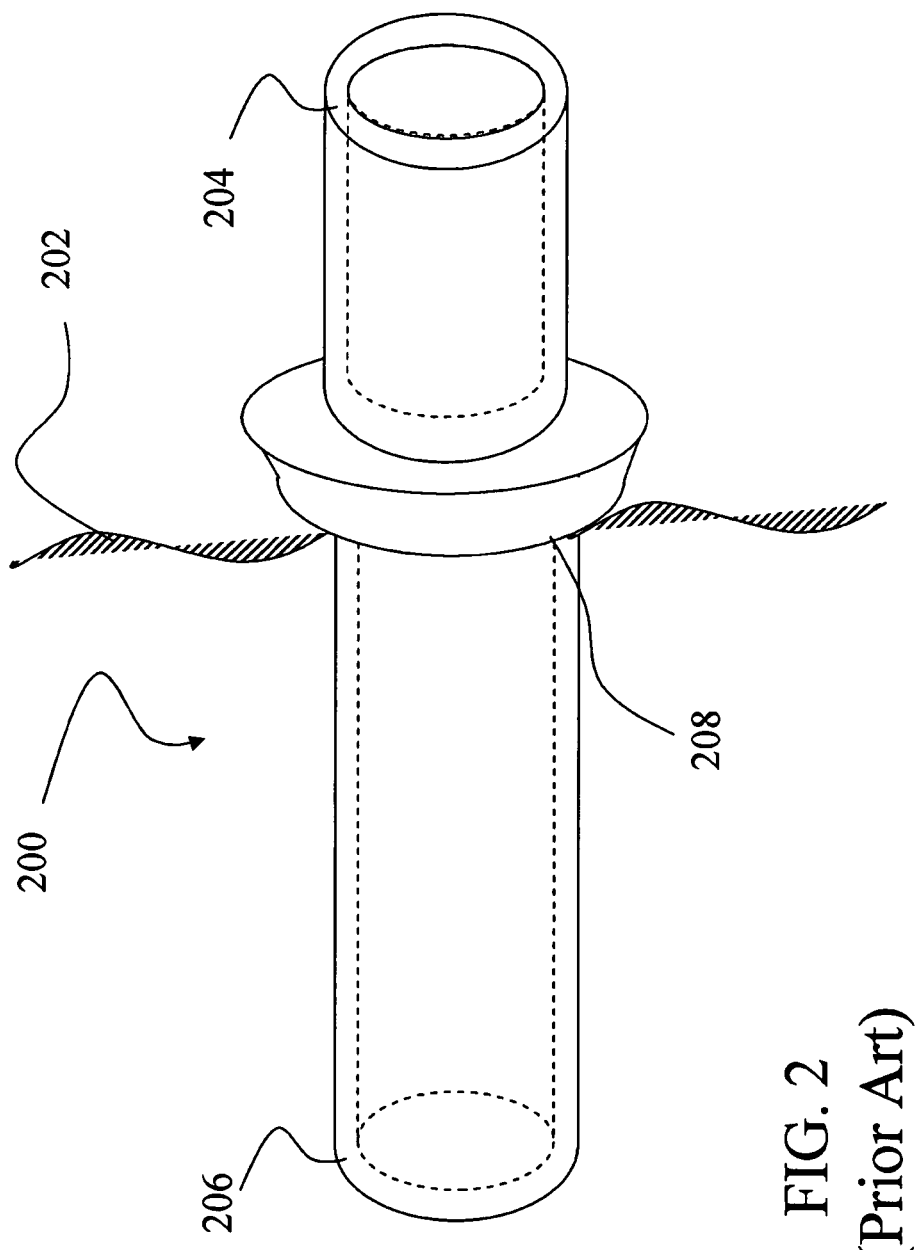
FIG. 2 illustrates a cannula inserted into a body cavity.
Figure 3:
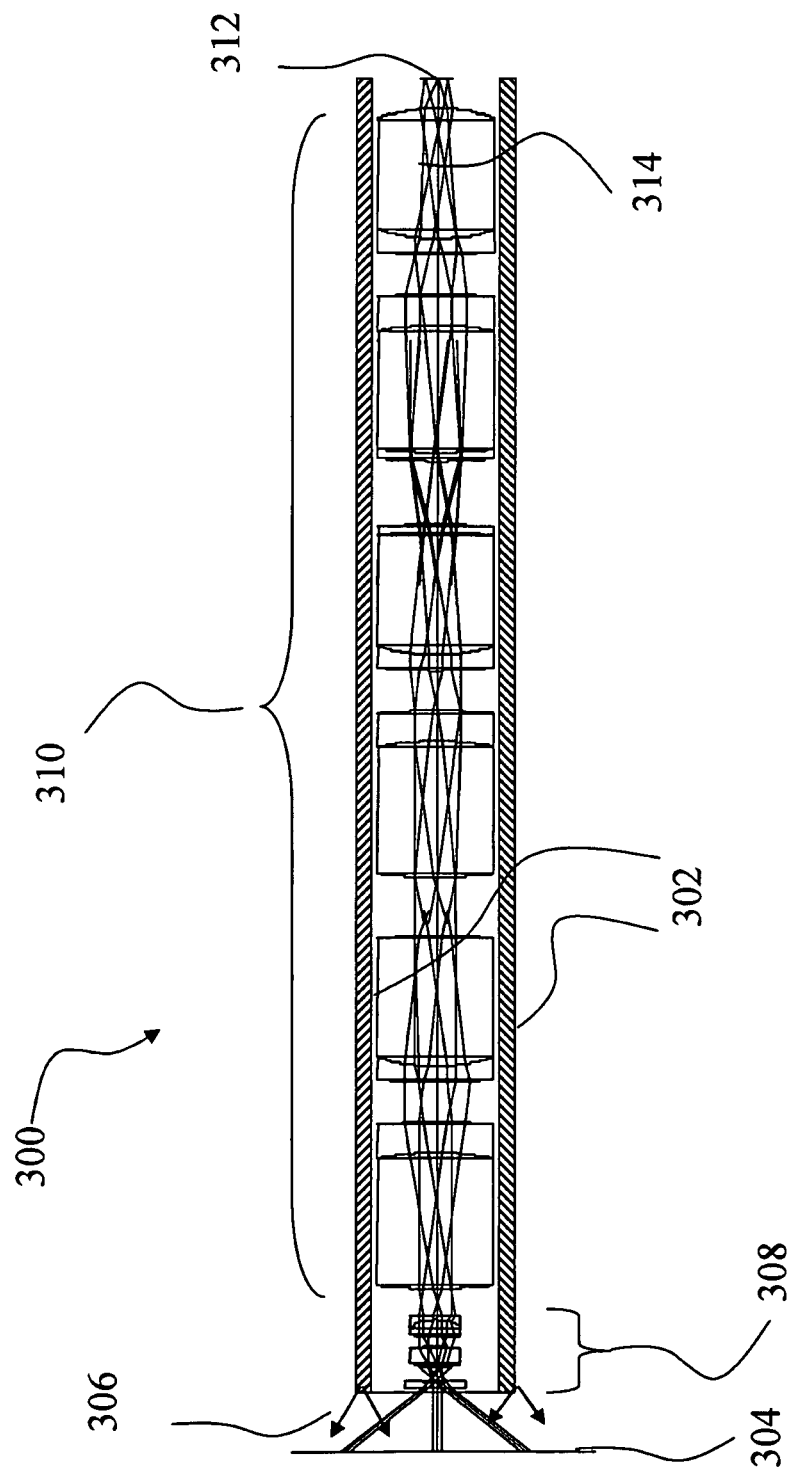
FIG. 3 illustrates a cross-sectional view of a typical zero degree, rigid endoscope with associated terrain for relay of the image through the length of the endoscope.
Figure 4:
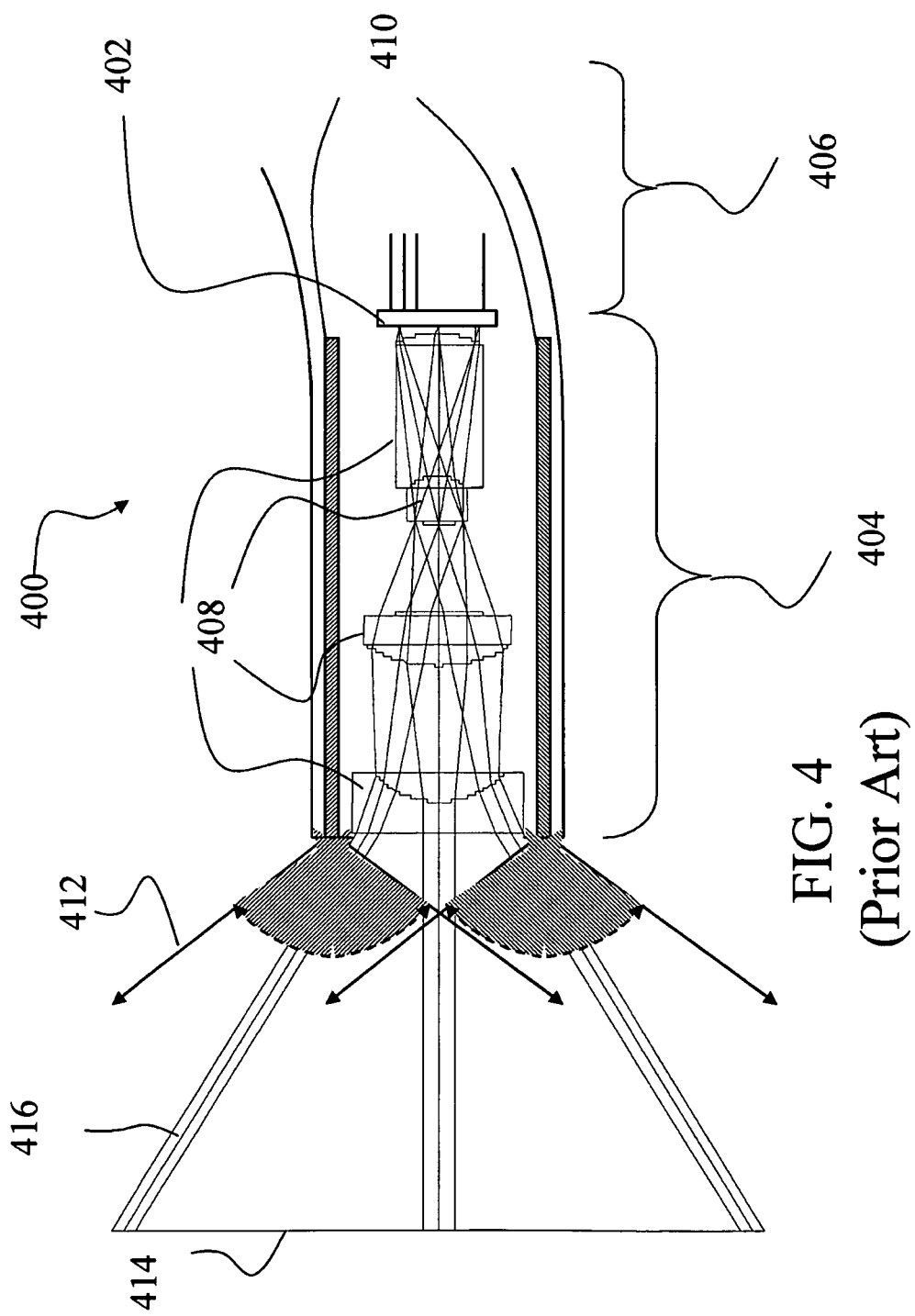
FIG. 4 illustrates a cross-sectional view of a zero degree typical flexible endoscope body (Chip on the Stick) with fiber optics illumination.

FIG. 6a shows an array of LED illuminators 604 (collectively referred to herein as "OE illumination module 604") distributed at the distal end 602 of a disposable endoscope or cannula body 600. Electrical drive currents for the LEDs and means of heat transfer using highly conductive material or micro heat pipes, to transfer the heat from LEDs to the proximal end of the endoscope or cannula body, can be provided within the body of the device. FIG. 6b represents a pluggable OE vision module 650, comprising a camera housing 601, within which is disposed one or more imaging lenses 608 and an image sensor 606. A clear optical window 603 is also provided to enclose the imaging lenses 608 and image sensor 606 within the camera housing 601. The pluggable OE vision module 650 can be attached to the distal end of a medical device, such as the Chip on the Stick articulating endoscope 400 of FIG. 4. Flex circuitry 605 can be used to provide power and control signals to the OE vision module 650 and to transmit imaging signals to a portable control and display unit 610. The portable control and display unit 610 generally includes a display screen, a housing, illumination and imaging control electronics, image processing electronics, and/or a power supply, such as a battery.

In some embodiments, flex circuitry 605 communicatively couples the portable control and display unit 610 to the OE vision module 650 to communicate power and control signals and imaging signals between the portable control and display unit 610 and the OE vision module 650. As such, the flex circuitry 605 serves as one example of a means for communicatively coupling the portable control and display unit 610 to the OE vision module 650. Alternately or additionally, flex circuitry 605 further communicatively couples the portable control and display unit 610 to OE illumination module 604 to communicate power and control signals between the portable control and display unit 610 and the OE illumination module 604. As such, the flex circuitry 605 further serves as an example of a means for communicatively coupling the portable control and display unit 610 to the OE illumination module 604.

Removable and pluggable OE illumination and vision modules with protective disposable covers, or implemented in a single use disposable medical device, can enable numerous advantages. For instance, a disposable medical device housing the OE module in a fully sealed sterile cavity can be disposed of after removal of the pluggable OE module, whereupon a new protected OE module can be plugged into a new sterile single use medical device housing for subsequent use, thereby eliminating the likelihood of contaminating body cavities in which the disposable medical devices are used.

Same type of removable and pluggable OE vision modules can be plugged into various designs of single use medical devices allowing for low cost variations in the medical device design and its functionality. The OE vision modules covered with a single use protective cover that is fully sealed can be made in various lengths and plugged into the distal tip of various medical devices, where the protective cover running the length of the inserted medical device can be disposed of after use, and a new protective cover seal on a new OE vision module can be plugged in for subsequent use.

Different OE vision modules, with various functionalities can also be plugged into the same type medical device depending on the procedure to be performed, providing means to choose from a variety of application specific medical vision capability. For instance, white light illumination or multi-spectral visible OE modules can be used for traditional imaging in the visible range.

A pluggable OE module with additional deep blue or UV illumination could be used to induce bio-fluorescence inside the body and detect spectral emission from the object, at the same time as the visible imaging, to gain further information regarding the object, such as the tissue type and identifying lesions. An IR illumination can be used in the OE vision module, to image inside tissue or through scattering substances or fluids, to give additional in depth view. Different UV, visible and IR wavelength illumination with varying penetration depths can be used for depth dependent imaging inside the tissue. Various spectral component captured 2D images can subsequently processed and put together to reconstruct a 3D view of inside the body.

Use of such removable and pluggable OE illumination and vision systems inside a cavity in the body replaces a variety of conventional instruments otherwise needed for the same purpose, such as an external light source, fiber light guides, means of transmitting the light to the desired object, imaging optics, and/or electronic cameras. Further, the removable and pluggable OE systems according to some embodiments of the invention can be used to perform tissue analysis inside the body, thereby eliminating the need for taking tissue for biopsy, and then performing a biopsy on dead tissue. This enables in vivo tissue analysis without the delay typically required to obtain a biopsy report, and further allows for real-time surgical procedures to be performed instead of possible follow-on surgical procedures after review of biopsy reports.

LED sources can provide illumination in a wide range of the electromagnetic spectrum, from UV, to visible and IR, where the individual LEDs in a specific spectral range can be independently controlled in time and the corresponding images independently processed based on individual captured frames. Each LED spectral component can be independently designed in the LED, or obtained with independent processing of each LED spectrum, via secondary photo-luminescence process on blue or UV LEDs, or using edge or band pass spectral color filters such as multilayer dielectric optical filter coatings. For imaging in the visible region, Red, Green, and Blue LEDs in primary colors can be used with or without other non-primary colors such as amber or cyan where the multiple spectral LEDs together form a white illumination.

By using multiple color LEDs and synchronizing a black and white image capture device to grab the synchronized color component images, the use of color camera chips or high resolution 3 CCD or 3 CMOS imaging devices are eliminated. In this case, a single CCD or CMOS image capture device is used to capture the three or more images in a time synchronized fashion, where each color component image takes advantage of the full image capture device resolution by incorporating all the pixels in each color image component. Simple black and white image capture devices are also cheaper to use, especially compared to 3 chip image capture devices, where in effect the resolution of a synchronized black and white imaging CCD or CMOS using synchronized color illumination provided by the LEDs is equivalent to a same pixel 3 chip image capture device.

Using color synchronized image capture devices also allows the use of much higher resolution image capture devices in chip on the stick cameras where space is limited at the distal tip of the endoscope for the image capture device. A variety of illumination configurations are possible using LED chips, where the uniformity, angle and extent of the illumination are freely controlled by the positioning and design of the LED light sources. Various illumination configurations are disclosed more fully in U.S. patent application Ser. No. 11/233,684.

In current endoscopic imaging systems where a white light illuminator is used, the illumination spectrum is determined by the light source and the optical path the light is transmitted through before reaching the object inside the body. Subsequently, a 3-color image capture device (e.g., a single-chip RGB camera or 3-chip RGB camera) captures the reflected light from the object according to its RGB filter set and image capture device spectral sensitivity. An image display unit in turn displays the captured RGB image according to its own color filters.

Infra Red (IR), Ultraviolet (UV) LEDs, or narrow spectral band VCSELs can be used based on their transmission characteristics in the medium of insertion, such as wavelength dependent penetration depth inside the medium or the effect they have on the object of interest (such as inducing auto-fluorescence). With an endoscope equipped with a full range of LED wavelengths, or a specific range of illumination wavelength, it is possible to obtain a full spectral image of the object by turning the various LEDs on and off at specified times, and in a controlled spectral range depending on application, while a time synchronized imaging process captures various spectral images based on the illumination at the time of capture. The LEDs can be distributed illuminators used with fixed image capture devices on the scope, introduced within the body of the disposable medical device as part of an OE vision module, or independently introduced inside the body with or without other medical devices.

LED illumination systems or removable and pluggable OE illumination and vision modules are modular, where one or multiple OE modules can be inserted into the body independent of one another, via separate medical device bodies, at the distal end of an endoscope, or incorporated at convenient and efficient locations on surgical tool tips or disposable cannulas, or other single use medical access devices such as Ear Nose Throat (ENT) speculum or cannula, providing an always sterile illumination and visualization of site inside the body. These single use medical devices incorporating the OE illumination and vision system could be battery operated or take power through the medical device that is plugged in externally.

Figure 7A:
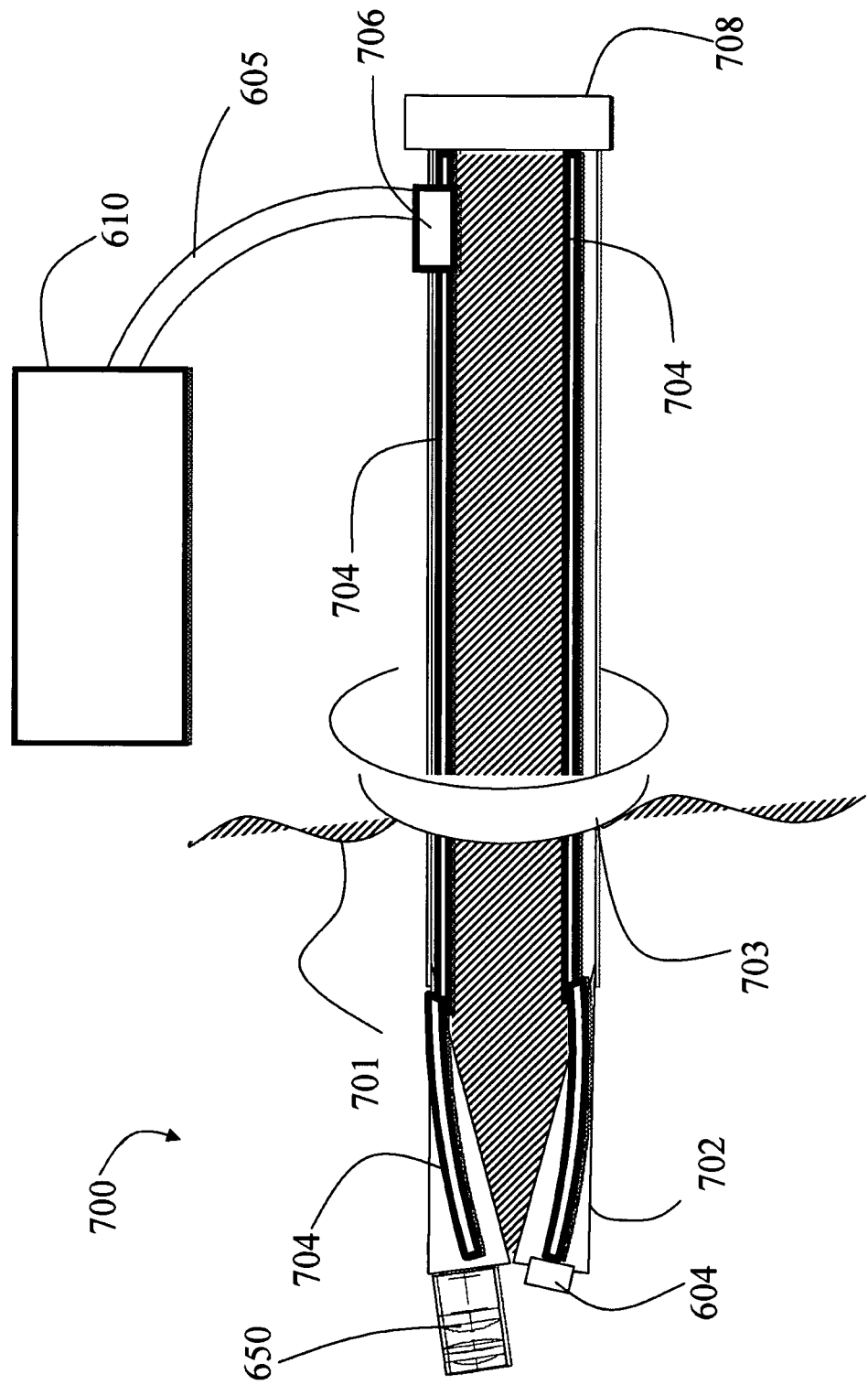
FIGS. 7a and 7b illustrate one example of the LED illumination and OE vision modules of FIGS. 6a and 6b incorporated at the expanding distal tip of a cannula.
Figure 7B:
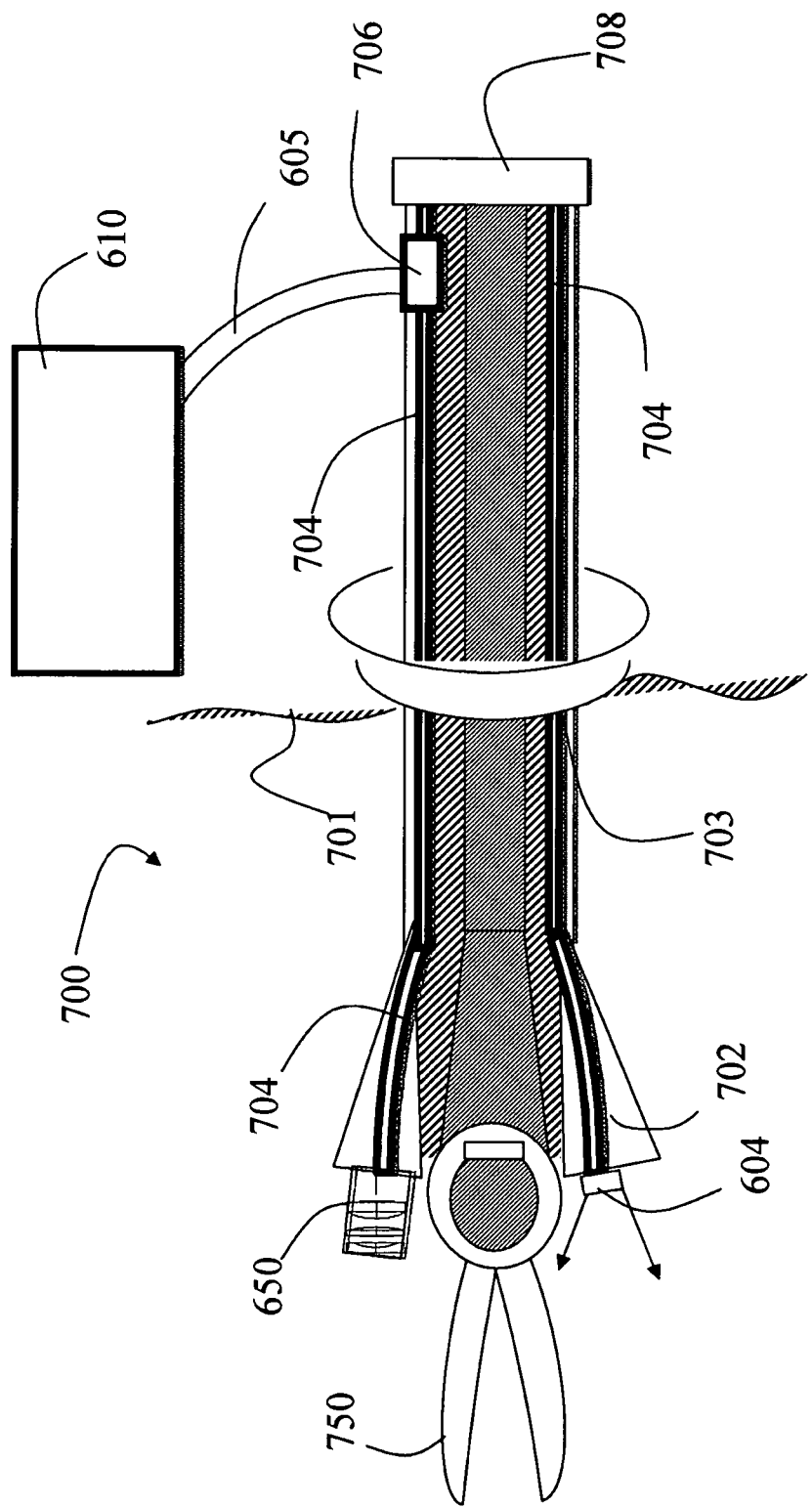

One embodiment of an OE illumination and vision module at the distal tip of a disposable cannula 700 is illustrated in FIGS. 7a and 7b. Cannula 700 is inserted through the skin 701, at an opening or incision 703. In this example embodiment, the distal tip of the cannula 700 is illuminated by white or color LEDs 604 mounted at the distal end 702 of the cannula, similar to the device in FIG. 6a. In addition, the OE vision module 650 of FIG. 6b is also mounted at the distal end 702 of the disposable cannula 700. The distal end 702 of the cannula 700 is made flexible in such a way that after insertion into the body through the incision 703, which can be made with or without the aid of a trocar, the distal tip 702 of the cannula can be expanded radially. Further, as shown in FIG. 7b, a surgical tool 750 can be inserted through the cannula 700 after the distal end 702 has been inserted inside the body and has been radially deployed. Electrical power to the LEDs 604 and OE vision module 650 is provided by the flexible electrical lines 704 that run along the cannula 700 body and terminate at an electrical connector 706 at or near the proximal opening 708 of the cannula 700. Outside the body, the flexible electrical cable 605 transfers power and control signals to the OE illumination and vision modules 604 and 650 at the distal tip of the cannula 700, from a portable control and display unit 610, while providing the imaging data from the camera unit 650 to the portable control and display 610.

Figure 8:
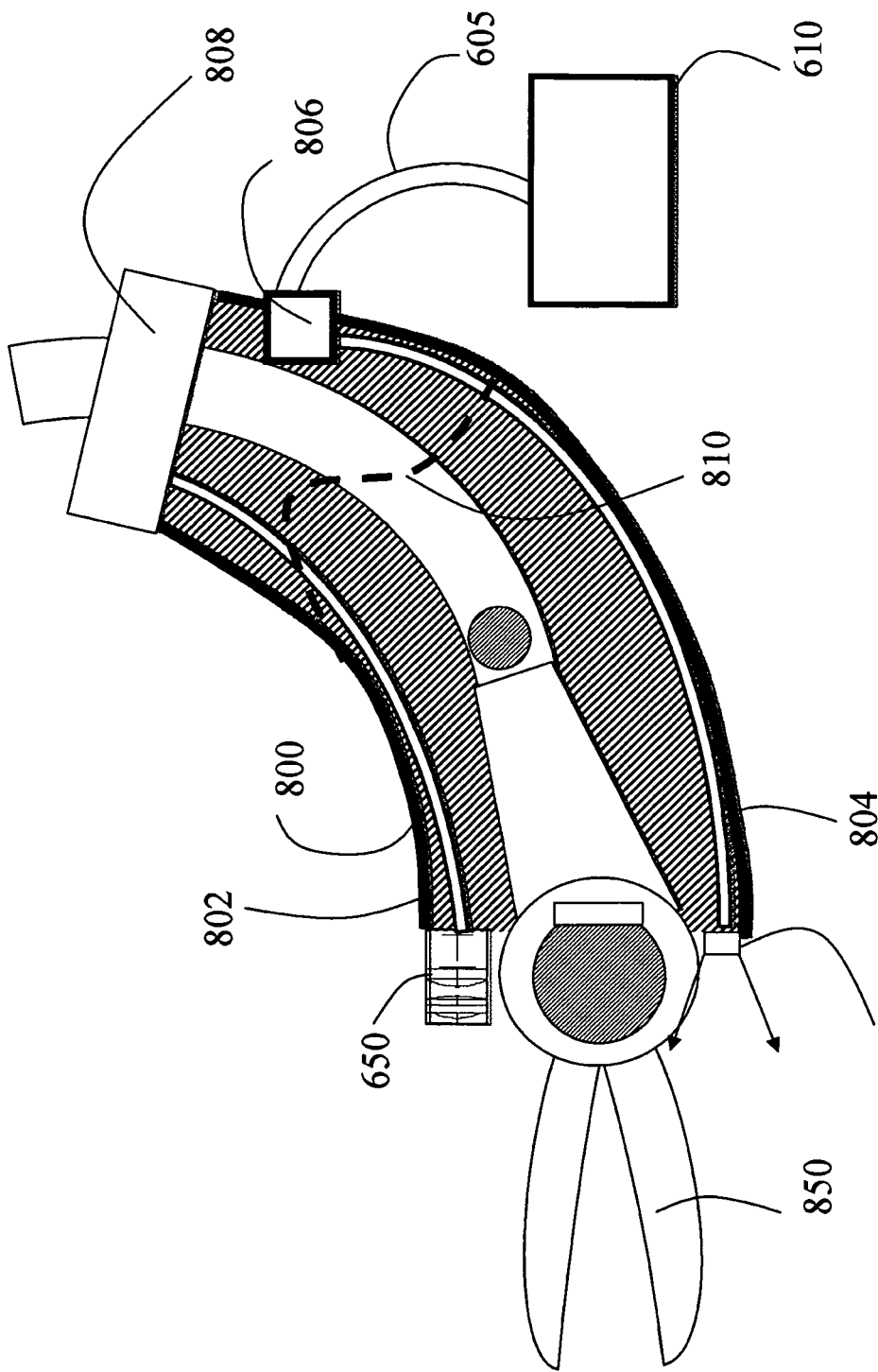
FIG. 8 illustrates another LED illumination and OE vision module incorporated at the distal tip of a flexible catheter.

FIG. 8 illustrates an example of OE illumination and vision modules 604 and 650 installed at the distal tip 802 of a flexible catheter 800 that can be inserted into a body's natural orifices. The OE illumination and vision modules 604 can be employed with catheters 800 of variable length, as represented by dashed line 810. As shown in FIG. 8, the catheter 800 includes a proximal opening 808, electrical connector 806 and flexible electrical lines 804 substantially running along the length of the catheter body.

Figure 9:
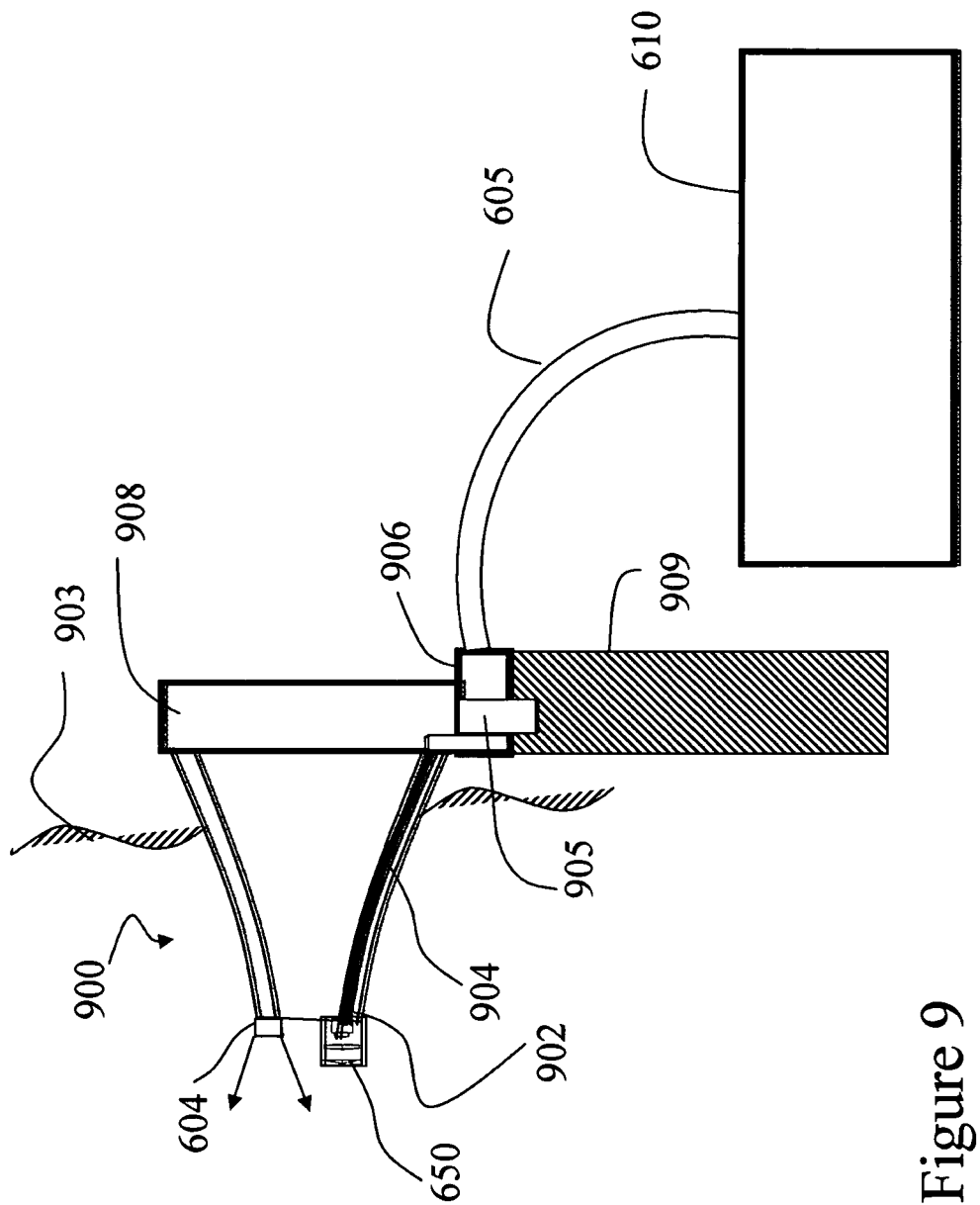
FIG. 9 illustrates yet another LED illumination and OE vision module incorporated into the distal tip of a disposable speculum of an otoscope.

FIG. 9 illustrates a disposable ear nose and throat (ENT) speculum 900 that is plugged into a handle 909. The speculum 900 incorporates OE illumination and vision modules 604 and 650, and includes a power connection 905 drawing power from batteries in the handle 909, or drawing external power from the portable control and display 610 via a power cable 605. The OE vision module 650 is connected to a distal tip connection structure 902, which caries power to the OE vision module 650 and transfers image data from the image sensor 606 (see FIG. 6A) to video cable 605 through electrical connections 904 within the body of the speculum 900. Video cable 605 can alternately or additionally provide external power from the portable control and display unit 610, which may be battery operated, to a complete otoscope unit consisting of the OE illumination 604 and the vision module 650.

By incorporating the OE vision module 650 at the distal tip of speculum 900, the speculum opening in proximal end 908 remains completely free for access to inside the body 903. For example, if the speculum is used to visualize and gain access into the ear canal, the examiner can use tools to remove earwax (cerumen) or apply an air puff into the ear to test the mobility of the tympanic membrane. Concurrently with insertion of a tool, the examiner can visualize the field indirectly using the OE vision module 650 without the inserted tool substantially hindering the examiner's view.

Removable and pluggable OE vision modules containing LED illumination or without LED illumination can be plugged into a variety of single use disposable or reusable endoscope, articulating and non-articulating surgical medical device bodies, used in a fixed position with respect to the medical device body, or deployed out of the medical device body once the medical device distal end is inside the body. Through the deployment process of the OE illumination and vision modules that are plugged into the distal tip of the medical device, the OE module can position itself outside the normal medical device volume, creating space inside the medical device and enabling further tool insertion through the cavity that the OE module was stored in during the insertion of the medical device into the body, thus allowing for further medical device functionality.

Figure 5:
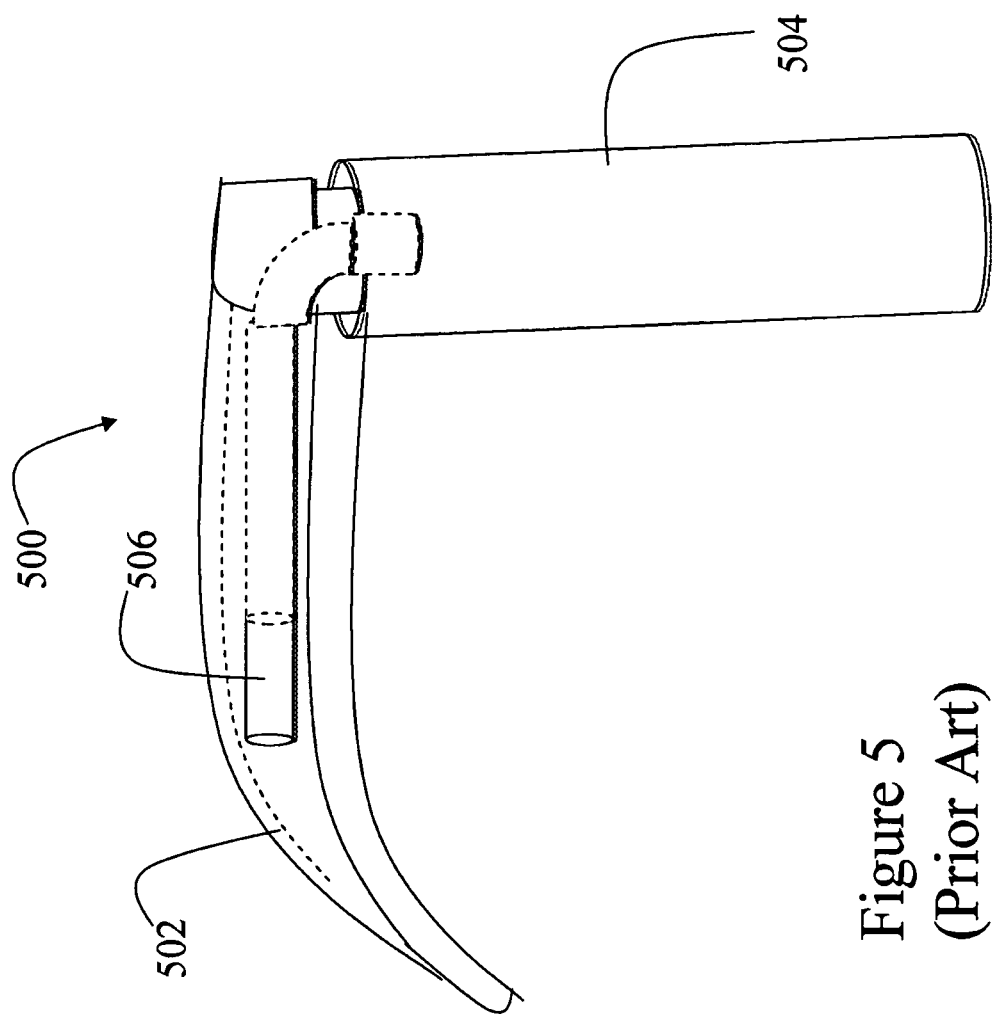
FIG. 5 illustrates a direct laryngoscope with attached Macintosh laryngoscope blade, equipped with a miniature lamp or fiber optic illumination for manual visualization of the larynx.
Figure 10:
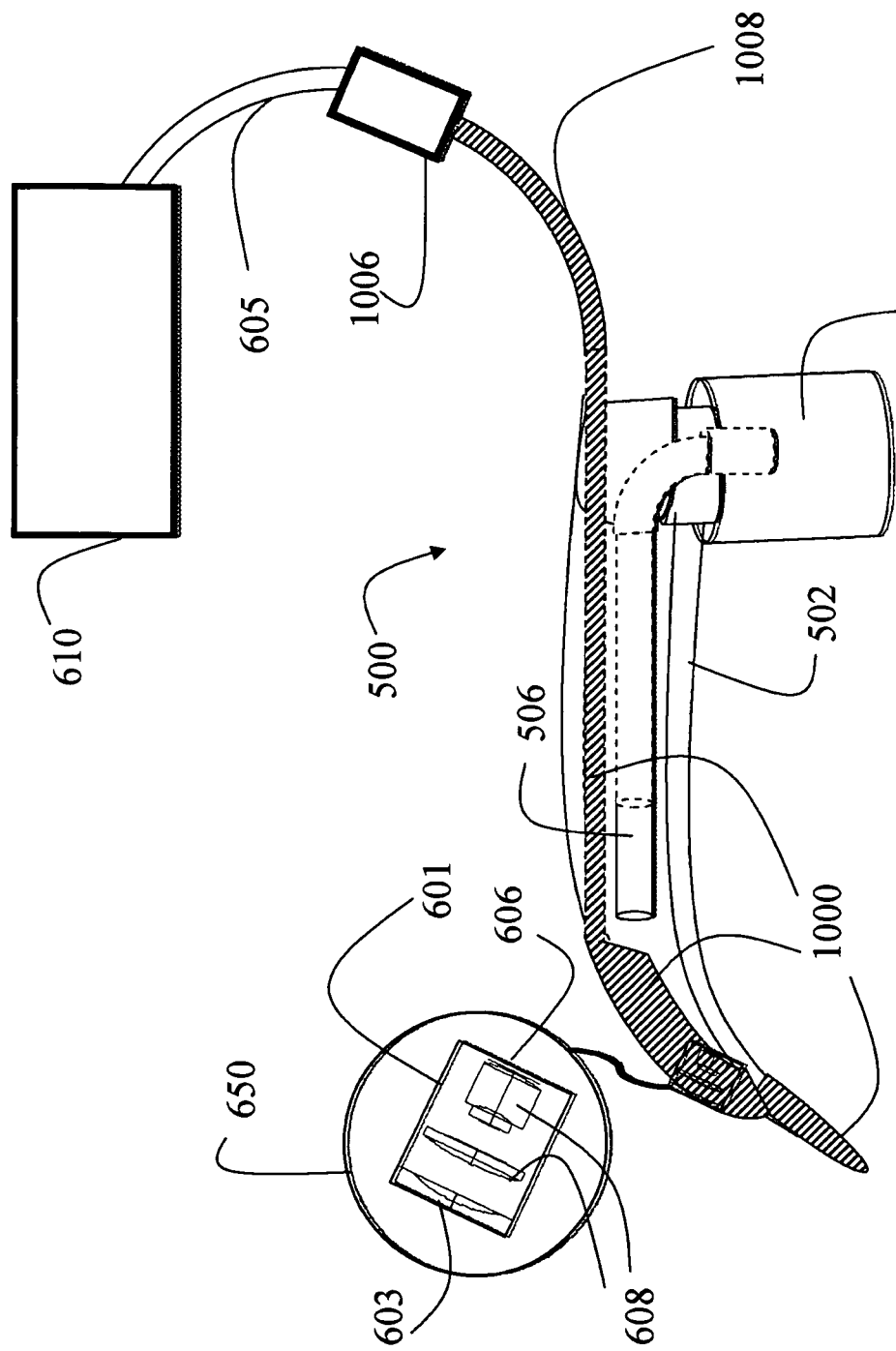
FIG. 10 illustrates an example embodiment of the fiber optic illuminated laryngoscope blade of FIG. 5 that is further equipped with the pluggable OE vision module or camera unit of FIG. 6b.

As an example of another fixed pluggable OE vision module onto the housing of a reusable medical device, FIG. 5 depicts a laryngoscope 500 with a handle 504 containing batteries for power, and a curved Macintosh type blade 502, equipped with fiber optic or lamp illumination 506 that is used for manual direct visualization of the larynx used in standard tracheal intubation. FIG. 10 illustrates a configuration that incorporates pluggable OE vision module 650 within a disposable device body 1000 that is plugged onto the lighted blade 502 of the Laryngoscope 500. As shown in the inset of FIG. 10, a molded optically transparent window 603 is disposed in front of the OE vision module 650 to provide wide access FOV for visualization. Window 603 can alternately or additionally be used as an optical imaging element for the OE vision module 650, where one or multiple lenses 608 are aligned in front of the image sensor 606.

Thermal pads can be disposed on top and bottom of the OE vision module 650 to make close contact with top and bottom surfaces of the OE vision module 650 and a separate heating resistor, if necessary, for efficient transfer of heat from the OE vision module 650 and the heating resistor to the window 603. The disposable device body 1000 can include a connector portion 1006 comprising electrical connections configured to mate with corresponding electrical lines that run through the device body 1000 along the length of the laryngoscope blade 502. The connector portion 1006 can be located at or beyond the laryngoscope handle 504 using a proximal flexible cable 1008.

In the embodiment of FIG. 10, the pluggable OE vision module 650 is fully housed in its own disposable molded device housing 1000. Although not required, in some embodiments, an external optical window (not shown) of the body 1000 allows image capture light to transmit inside the OE vision module 650. Heat from a heating resistor and/or the OE module body 601 is conducted to the window 603 of OE vision module 650, as well as being coupled through optional heat conducting pads to the external optical window of device body 1000. The heat can keep both windows warm to avoid condensation and fogging during use. The OE module 650 can be turned on a short while before a procedure to warm up the windows if the laryngoscope blade 502 is stored in a cold environment.

The configuration of FIG. 10 can convert a traditional direct laryngoscope to a video laryngoscope, which may be useful for intubation processes that encounter difficulty (difficult airway cases) and/or in other situations. Alternately or additionally, the configuration of FIG. 10 can provide the means for multiple viewing and recording of an intubation process concurrently with the direct view laryngoscopy, facilitating instruction and teaching of intubation procedures.

The pluggable OE vision module body 1000 can be made to occupy minimal extra space on the direct laryngoscope by using the outer space between the illuminator 506 and the upper blade body for the flex wires within the body 1000 of the disposable module. The OE vision module 650 can be configured to be placed in the central area near the distal tip of the laryngoscope blade, pointing towards the tracheal opening and coinciding with the direction of view of the illumination, without taking any space on the laryngoscope blade where the tube is inserted and the channel provided for direct viewing. The distal tip of the laryngoscope blade can be used to fit into the OE vision module body 1000, for securing the OE vision module 650 in place, and the proximal end of the laryngoscope blade can be used for a locking mechanism of the pluggable OE vision module body 1000.

In case of surgical laryngoscopy where surgery is performed using the laryngoscope 500, or in difficult airway cases such as in the case of an infant patient, such pluggable OE vision systems 650 can not only be made in minimal size, but can alternately or additionally house two miniature camera systems with an extended dual camera connection 1006 for stereoscopic view of the surgical sight and 3D viewing of the tracheal opening for extra precision guiding visual depth clues.

Incorporating solid state OE illumination and vision modules in endoscope and surgical device bodies provides a desirable cost advantage over conventional lamp and fiber guide systems, as it replaces the expensive light sources, long fiber optic light guides to transfer illumination light from the light source to the scope, and the illumination light guides inside the scope as well. Low level power is needed for the LED light sources, image sensors and drive electronics, thus the electrical connection of the OE illumination and vision module is also much easier.

Only electrical power and LED control signals need to be provided for the endoscope, eliminating the heavy and bulky fiber optics illumination cable connection to the scope, increasing the maneuverability and durability of the endoscope. OE illumination and vision modules are also more robust to shock and vibrations or extreme environmental conditions than fiber optic illumination and external camera systems.

In addition to the embodiments of FIGS. 7a-10, articulating and/or deployable embodiments are possible for effective illumination and imaging of a surgical site. In deployable embodiments, such as the embodiment of FIGS. 7a and 7b, the OE illumination and vision modules are deployable from an insertion position in which they are held within the insertion body or within a close profile of the insertion body, to an operational position where they are conveniently pointed to an object of interest. In operational position, the illumination light as well as the imaging FOV can be directed to the surgical site from beyond the endoscope body, where deployment of an OE module holding structure positions the vision module off axis from the axis of the insertion body, possibly increasing the functionality of the surgical device as well.

Figure 11A:
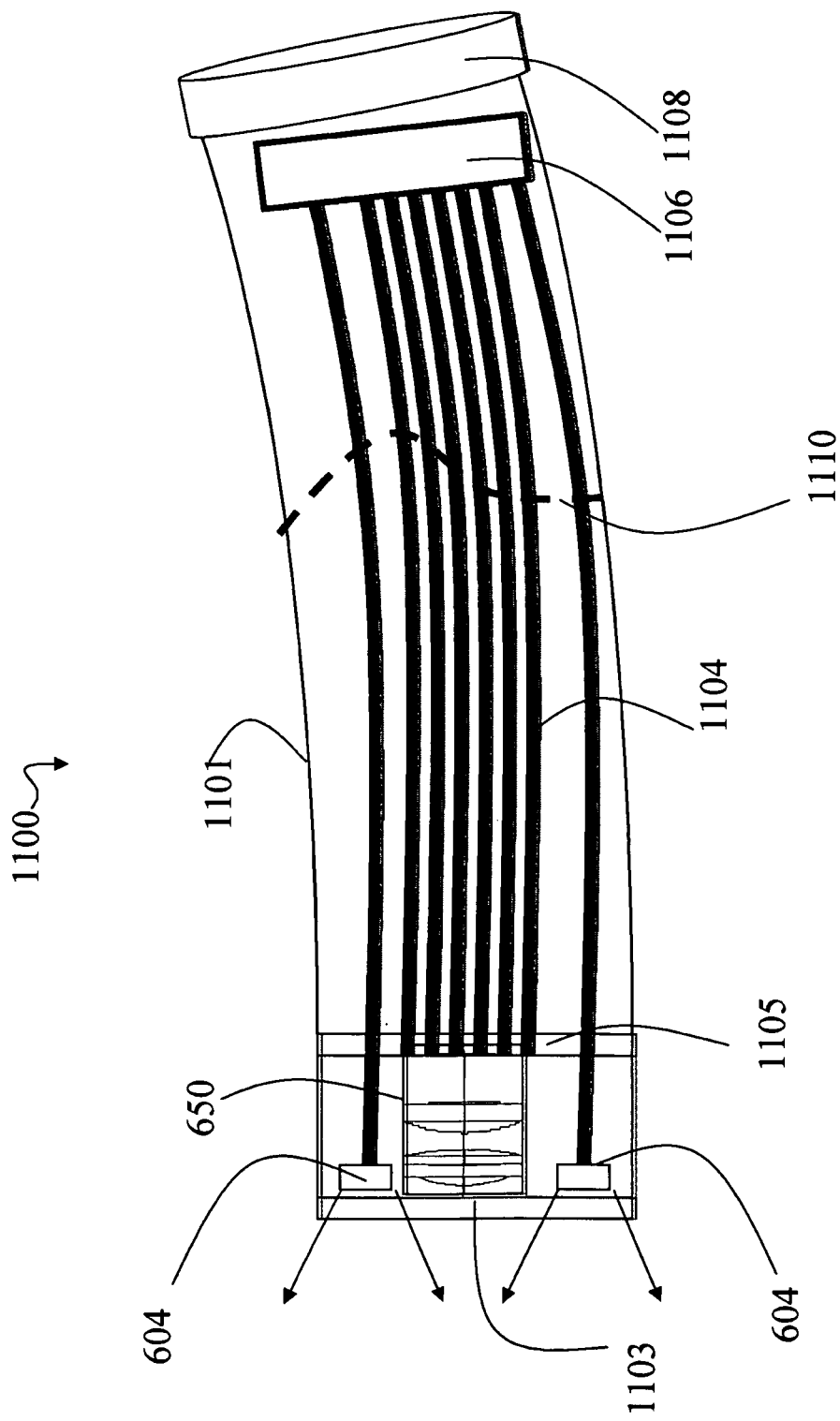
FIG. 11a illustrates an example pluggable OE illumination and vision module with electrical lines running through a flexible jacket through which a medical control device can be inserted.

FIG. 11a discloses a pluggable module 1100 comprising an OE illumination 604 and vision module 650 incorporated in a single use, flexible, protective cover or jacket 1101, with a flat distal optical window 1103 sealed in the protective cover 1101. The flexible protective cover 1101 can be made in variable lengths, denoted by the dashed lines 1110 in FIG. 11a and 11b, and houses the necessary electrical connections 1104 to the OE illumination 604 and vision module 650 from an electrical connector 1106.

In some embodiments, the protective cover 1101 and optical window 1103 are fully sealed with the optical window 1103 forming a substantially airtight seal with the protective cover 1101. Alternately or additionally, moisture can be substantially removed from within the cavity defined by the protective cover 1101 and optical window 1103 such that the cavity is filed with substantially dry air. Optionally, although not shown, one or more moisture absorbing elements can be disposed within the cavity defined by the protective cover 1101 and optical window 1103 to maintain the air within the cavity substantially devoid of moisture.

Figure 11B:
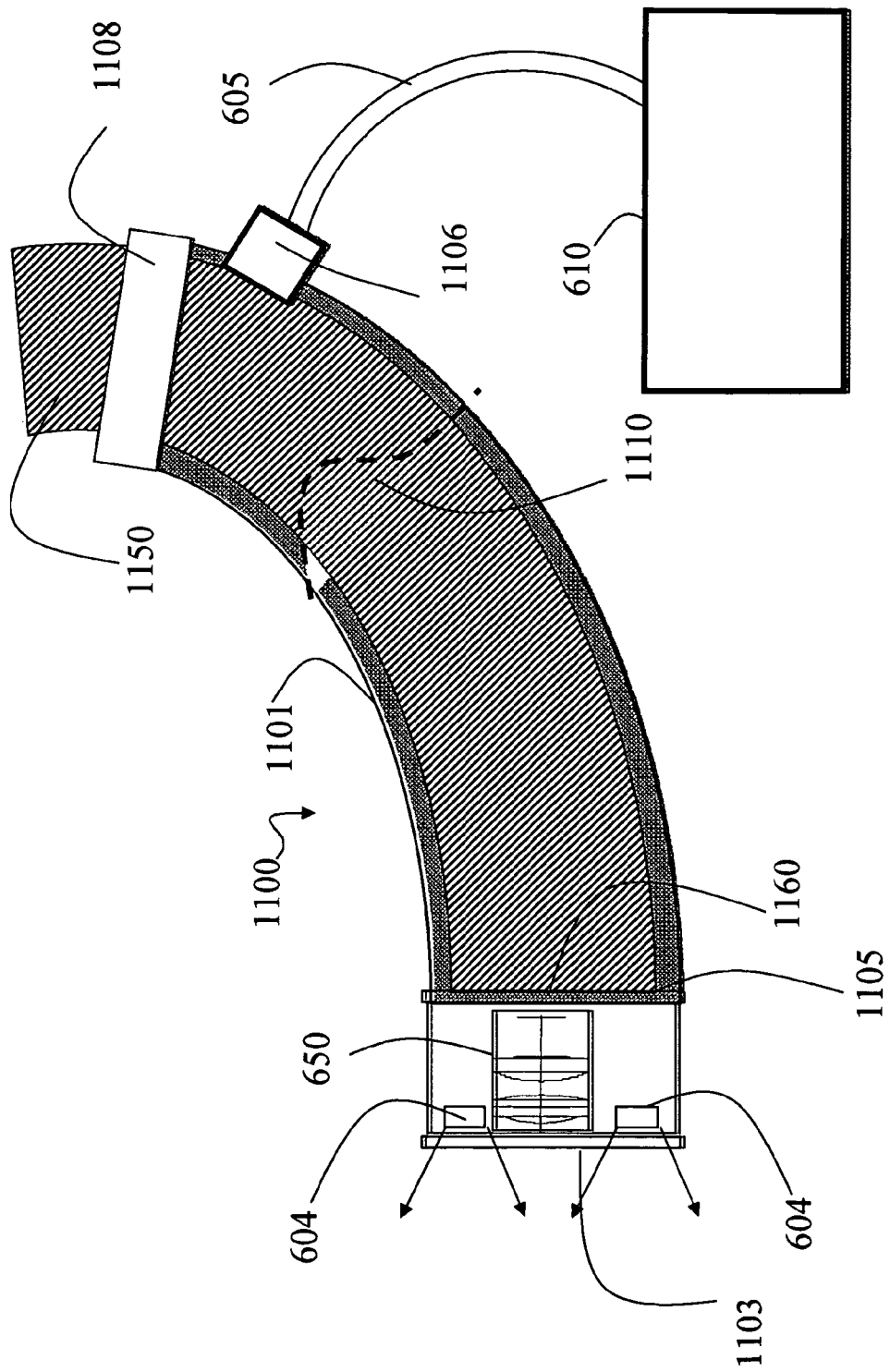

In some embodiments, the flexible body 1101 includes a proximal opening 1108 operable to receive a body 1150 therein. For example, FIG. 11b represents the insertion of the body 1150 into the flexible body 1101 of the pluggable module 1100. The body 1150 can be rigid, flexible, formed, or articulating. The body 1150 and pluggable module 1100 form a curved, flexible, or articulating endoscope. When the body 1150 comprises an articulating device, appropriate mechanical connection can be made between a base 1105 of the rigid tip of the pluggable module 1100 and a distal reference surface 1160 of the body 1150 to allow full one-to-one articulation of the pluggable module 1100 with the body 1150 at the distal tip.

The portable control and display unit 610 is connected to the pluggable module 1100 using electrical cable 605, which electrical cable 605 connects to the electrical connector 1106 near proximal opening 1108 of the flexible jacket 1101.

FIGS. 12a-13b illustrate examples of endoscopes 1200, 1300 comprising pluggable flexible bodies 1201, 1301, respectively. The endoscope 1200 includes LED array modules 1202, while the endoscope 1300 includes LED array modules and light reflectors 1202. A dynamic deployment of the LED array modules 1202 and/or light reflectors 1302 can be achieved with a cable actuated deployment mechanism provided at the distal tip of endoscopes 1200 and 1300, respectively.

Figure 13A:
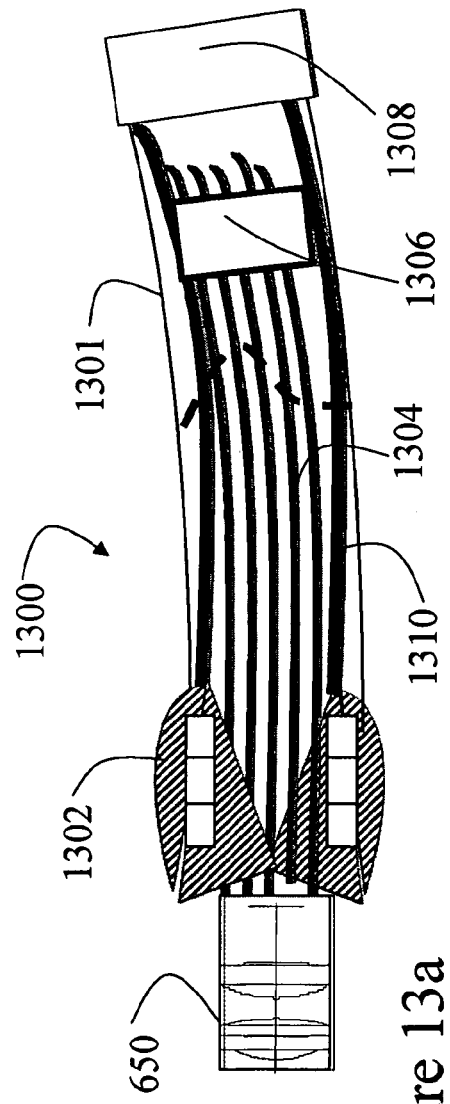
FIGS. 13a and 13b illustrate an example of an LED illumination system that employs outward deployment of a pair of shaped reflectors in front of a pluggable OE illumination module to provide illumination to a corresponding OE vision module's direction of view.
Figure 13B:
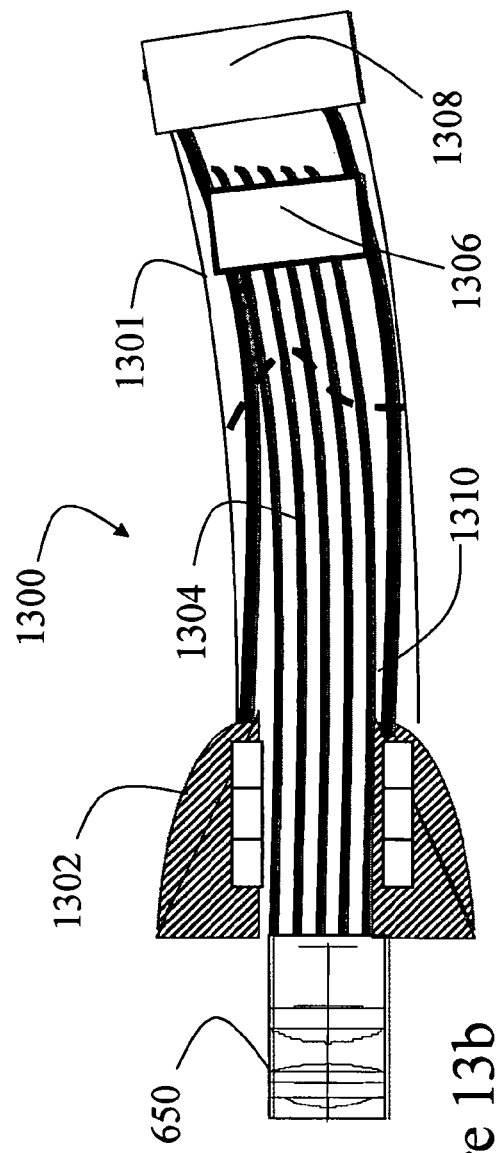

In FIGS. 12a and 13a, each of the LED array modules 1202 and light reflectors 1302 are in an "off" or insertion position. To deploy the LED array modules 1202 or light reflectors 1302, the LED array modules 1202 and light reflectors 1302 are flipped over to the side of the endoscope tip using actuation cables 1210 and 1310 actuating the deployment mechanism inside the flexible body 1201 and 1301. FIGS. 12b and 13b illustrate the LED array modules 1202 and the light reflectors 1302 in a deployed or "on" position. The deploying LED array modules 1202 and/or light reflectors 1302 can each separately comprise a single moving part or multiple components that move independently or synchronously with one another to take a final in-use "on position" position and form, such as components of a multi-faceted reflector expanding to form a parabolic shape or another convenient shape in front of the LED sources.

In alternate embodiments of all of the pluggable OE illumination and vision modules in the form of cannulas, catheters, and other devices described above that use LEDs for illumination, Solid State Laser Diodes (LD) or VSCELs can alternately or additionally be employed within the OE illumination and vision module or independently at the distal end of pluggable single use devices. For instance, Infrared (IR) Imaging employs IR solid state light sources to illuminate intra-vein or close tissue diagnostic and surgical procedures. IR detectors and special image sensors with modified optical filters in front of their pixels can be employed within OE vision modules for through tissue and blood imaging along with infrared light sources that have appreciable penetration depth in human tissue, blood or other bodily fluids. such as urine. Using a high intensity IR source at the surgical or examination site with control over the intensity, radiation pattern, and the direction of illumination can help with critical surgical procedures inside the vein, heart and other body organs.

By placing the illumination light sources at close proximity to the object inside the body in diagnostic or surgical procedures, the losses in conjunction with the transmission of light from the external source to the surgical site are eliminated. Thus, light sources that have equal efficiency in converting electrical power to useful light, can be operated in much lower input power, eliminating the need for sophisticated power and heat management. Power and control signals transmitting through appropriate wires and flex circuitry, can be easily routed along the tool or endoscope body to the light source and OE vision module.

Other embodiments of pluggable OE illumination and vision module can be obtained by clipping the pluggable module 1100 of FIG. 11*a* onto a simple handheld pen-like medical tool. Various illumination sources (e.g., LEDs, solid state sources, or VCSEL sources) of various spectral characteristics (UV, visible, IR, narrow or wide spectral band) can be used in the module to apply different functionality to the handheld device. For example, the handheld device can be used for detection of pre-cancerous cells by inducing biofluoresces using blue light illumination in the mouth or other bodily cavity, with or without use of contrast agents. Such hand held devices can be equipped with the electrical connection 1106 at the proximal end for power and imaging signal transfer, or can be battery operated via a portable control and display unit 610.

In some embodiments of the invention, multiple OE vision modules 650 are employed within a single pluggable module to obtain a combined hyper field of view of an imaging site. Alternately or additionally, inputs from two cameras can be obtained for stereoscopic viewing. In these and other embodiments, the portable control and display unit 610 can be used to house all the control electronics necessary to power the OE vision module(s) 650, control illumination and imaging functionality, data transmission control, image processing and/or display functionalities. For instance, the portable control and display unit 610 can include illumination and imaging control electronics that provide illumination and/or imaging control of the OE illumination module 604 and/or the OE vision module 650. Alternately or additionally, the portable control and display unit 610 can include image processing electronics that provide image processing of image data received from the OE vision module 650.

The portable control and display unit 610 can be a portable display unit used in a fixed position in a medical facility, or as a mobile application with an LCD, plasma, or other display unit capable of displaying 2D or 3D (stereoscopic) images. The portable control and display unit 610 can alternately or additionally be worn by a user, with a wired or wireless connection to the input devices (e.g., the OE vision module(s) 650), where the user can observe 2D or 3D stereo images and video conveniently by looking at the display mounted on an arm of the user, hanging from a neck of the user, or otherwise mounted to the user.

The portable control and display unit 610 can be electrically powered using a power cable, or it can be electrically powered using a rechargeable or disposable battery. In some embodiments, the electrical power supply of the portable control and display unit 610, whether from a power cable or battery, provides power for the portable control and display unit 610 as well as the OE illumination and vision modules 604, 650 to which the portable control and display unit 610 is attached via cable 605. Single or multiple OE illumination 604 and vision modules 604, 650 can be connected to the portable control and display unit 610, which portable control and display unit 610 can be configured to provide synchronized control of complete illumination and image capture. The portable control and display unit 610 could also provide means for local and transferable means of image and video storage, with magnetic and/or electrical storage devices within its housing. A user interface can be provided on the portable control and display unit 610 and may include hard or soft electronic keys, a mouse or joystick, a touch screen, and/or voice activated command electronics. The user interface can be employed to adjust, control, display, process, transfer, store or retrieve the image and video data. The portable control and display unit 610 can alternately or additionally comprise a multifunctional unit that is used as both a general portable medical display and one or more of: a cell phone, a mini computer with wireless capabilities, a GPS unit, a personal digital assistant (PDA), a note-taking device, a dictation device, a video conferencing device, or the like.

The user interface devices described above, including hard or soft electronic keys, a mouse or joystick, a touch screen, and voice activated command electronics all serve as examples of input and/or output means that can be included in the portable control and display unit 610. The portable control and display unit 610 can alternately or additionally include computing means, such as a processor, microprocessor, controller, or the like. Alternately or additionally, the portable control and display unit 610 can include cellular communication capabilities and/or wireless connectivity.

In some embodiments that include stereoscopic or 3D image capture, portable control and display unit 610 displays time-synchronized alternate left and right frames of the video from the medical device, where a pair of time-synchronized LCD shutters in front of the user's left and right eyes allow each eye to see the corresponding stereoscopic images. In such embodiments, the user can wear 3D-viewing time-synchronized shutter glasses while viewing the 3D displayed data, as the 3D-viewing LCD shutter glasses are time-synchronized with the portable control and display unit 610 via a timing signal received via wireless (e.g., IR connection) or hardwired connection to the portable control and display unit 610.

The portable control and display unit 610 may comprise a flat panel LCD screen, plasma screen, or other suitable screen. Alternately or additionally, the portable control and display unit 610 can have multiple positioning and attachment possibilities, depending on its size, the type of medical device its used with, the type of medical procedure, the location the procedure is performed, and the type of user interface necessary. In fixed office or surgical environments, the portable control and display unit 610 can be fixed to a wall or mounted on an IV post, or can be hung from a frame structure, with tilt and rotation capabilities and in a removable and portable form. Alternately or additionally, a fixed control and display unit can be employed to control OE illumination and vision modules 604, 650 and/or to display image data captured by OE vision modules 650.

Figure 14A:
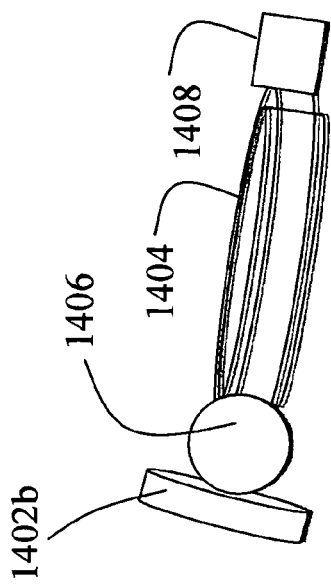
FIG. 14a illustrates one example mounting mechanism for a portable display.

FIG. 14*a* discloses one embodiment of a mounting mechanism 1402*a* that can be employed to mount the portable control and display unit 610 to an IV post, the floor, a user, or other structure. In the example of FIG. 14*a*, the mounting mechanism 1402*a* comprises a U-shaped sliding mechanism disposed on the back of the portable control and display unit 610 housing, although other configurations can alternately be employed.

Generally, the mounting mechanism 1402*a* is configured to removably engage a complementary mounting mechanism on a structure for removably mounting the portable control and display unit 610 to the structure. For instance, in FIG. 14*a*, the mounting mechanism 1402*a* is configured to removably and slidably engage a complementary disk mating mount unit 1402*b* (FIGS. 14*b*-15*c*) to facilitate simple and quick attachment and/or removal of the portable control and display unit 610 to virtually any structure equipped with a disk mating mount unit 1402*b*. Examples of structures equipped with disk mating mount units 1402*b* follow in FIGS. 14*b*-15*c*.

Figure 14B:
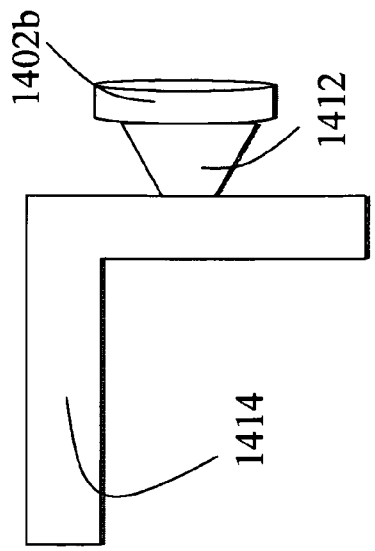

For example, FIG. 14*b* illustrates a round clamp that allows portable control and display unit 610 to be attached to an IV post. More particularly, the round clamp of FIG. 14*b* comprises a ring clamp 1404, lockable rotation and pivot mechanism 1406, and clamp and lock mechanism 1408. The ring clamp 1404 is configured to receive an IV post. The clamp and lock mechanism 1408 is configured to clamp and lock the ring clamp 1404 to the IV post. The lockable rotation and pivot mechanism 1406 is configured to lockably rotate and pivot to allow the portable control and display unit 610 to be selectively repositioned by a user. The disk mating mount unit 1402*b* is connected to the lockable rotation and pivot mechanism 1406 and, in this and other embodiments, is configured to slide into the mounting mechanism 1402*a* mounted on the back of portable control and display unit 610 to removably engage the portable control and display unit 610.

Figure 14C:
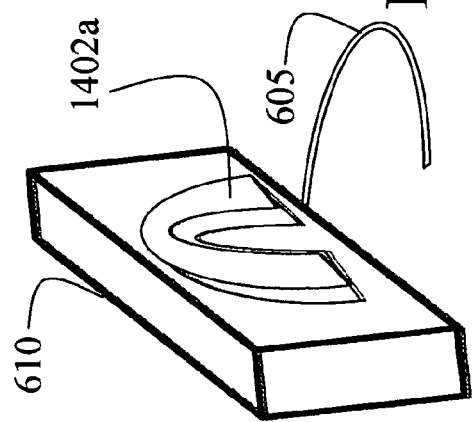

FIG. 14*c* illustrates an adjustable triangular mount 1410 that allows the portable control and display unit 610 to be positioned on a floor 1411 or other surface. Disk mating mount unit 1402*b* is connected to the triangular mount 1410. In some embodiments, the portable control and display unit 610 can be positioned at an adjustable viewing angle using the triangular mount 1410 of FIG. 14*c*.

Figure 14D:
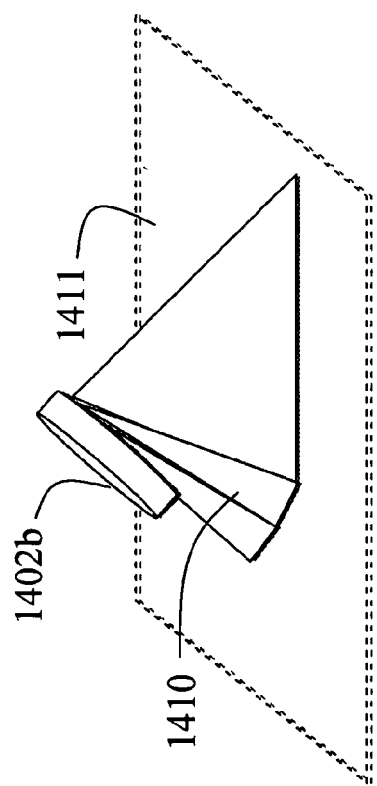

FIG. 14*d* illustrates a hanging mechanism 1414 with a disk mating mount unit 1402*b* connected via a tilt mechanism 1412. The hanging mechanism 1414 can have virtually any configuration that allows the hanging mechanism 1414 to hang from one or more structures, such as a horizontal bar, table top, shelf, or the like. The tilt mechanism 1412 is configured to tilt in one or more directions to allow a user to selectively reposition the angle of view of the portable control and display unit 610 relative to the hanging mechanism 1414.

Figure 14E:
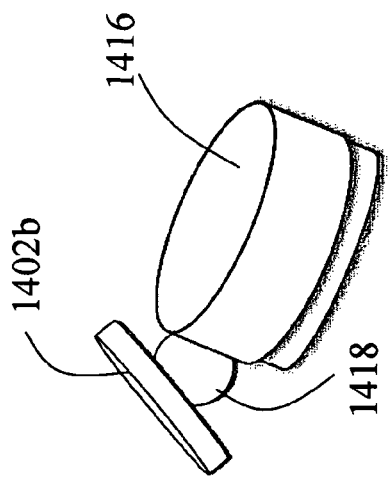
FIGS. 14e-14f illustrate adjustable mounting mechanisms for the portable display of FIG. 14a that can be attached to the handle of the laryngoscope of FIG. 10.
Figure 14F:
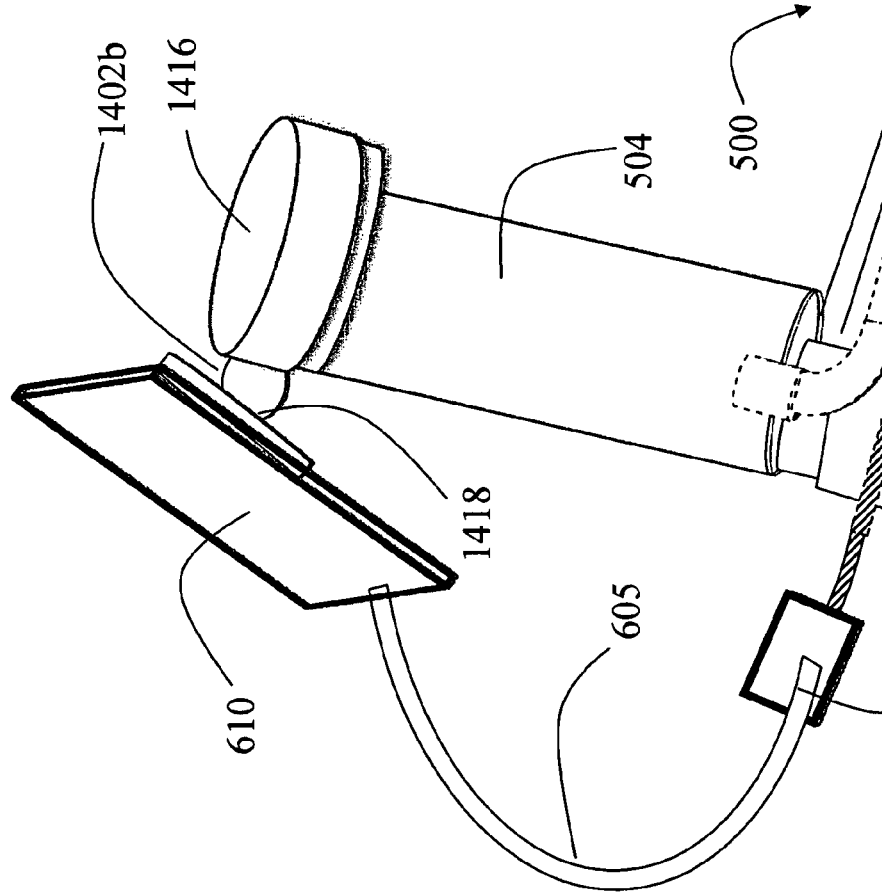

FIG. 14*e* illustrates a cap mounting mechanism 1416 comprising a pivot and rotation mechanism 1418 connected to a disk mating mount unit 1402*b*. The cap mounting mechanism 1416 is configured to be set on the bottom of a handheld medical device handle, such as the laryngoscope 500 handle 504 illustrated in FIG. 14*f*. In the example of FIG. 14*f*, the pluggable OE vision module 1000 of FIG. 10 is plugged onto blade 502 with lighting mechanism 506. The pluggable OE vision module 1000 is also connected to the portable control and display unit 610 through electrical cable 605 and electrical connector 1006.

Figure 15D:
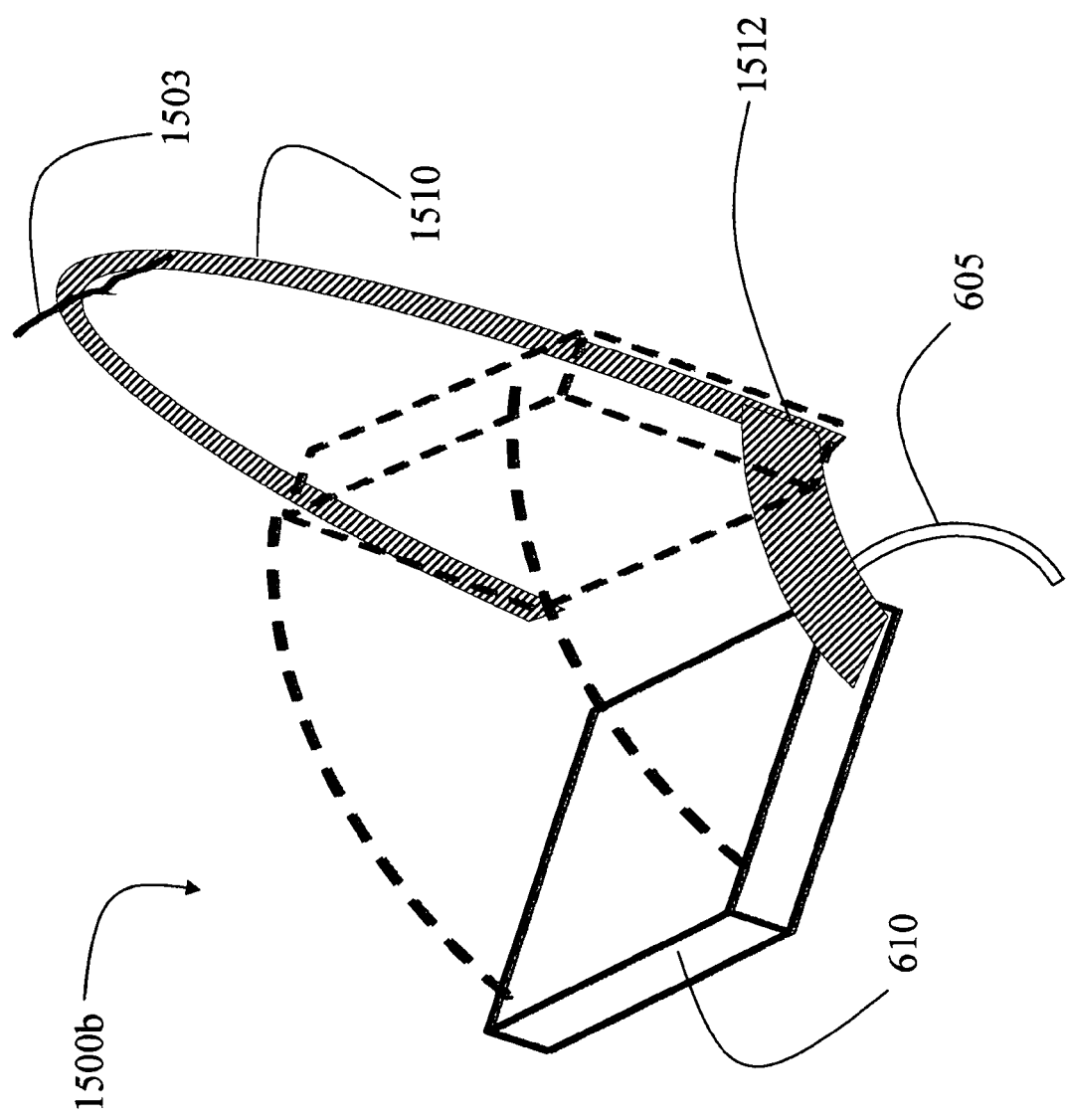
FIG. 15d illustrates an embodiment of a wearable and portable display that is configured to hang on a user's neck and fold outward.

FIGS. 15*a*-15*e*, illustrate "wearable" configurations of the portable control and display unit 610 where the portable control and display unit 610 is attached to the arm or wrist of a user via a wearable attachment device. In more detail, FIG. 15*a* illustrates a wearable attachment device comprising a resiliently deformable bracelet 1502, such as a memory shaped bracelet, that is connected to a disk mating mount unit 1402*b*. The bracelet 1502 can be unfolded to prepare for use, and then snapped to take its round shape (dictated by the memory shaped strip inside the bracelet 1502) around the user's arm or wrist.

FIG. 15*b* illustrates a wearable attachment device comprising a wide elastic band or Velcro strip 1506 that is connected to a disk mating mount unit 1402*b*. Similar to the bracelet 1502 of FIG. 15*a*, the wide elastic band or Velcro strip 1506 can be employed for adjustable attachment or wearing of the portable control and display unit 610 on the arm or the wrist of the user.

The wearable attachment devices of FIGS. 15*a* and 15*b* can alternately or additionally be equipped with adjustable (one- or two-way) tilt mechanisms 1504 that can be adjusted to allow convenient direct viewing of the display by the user during use. The wearable attachment devices of FIGS. 15*a* and 15*b* can be worn over a user's clothing during or before with or without physical connection to the OE vision modules 650 or other input devices.

Alternately or additionally, as shown in FIG. 15*c*, the wearable attachment devices of FIGS. 15*a* and 15*b*, or other wearable attachment devices, can include an additional protective and shielding mechanism 1508. The protective and shielding mechanism 1508 can be unfolded from the surface of portable control and display unit 610 to prevent glare on the portable control and display unit 610 when used in the outdoors or other environments. The portable control and display units 610 employed in conjunction with the wearable attachment devices of FIGS. 15*a*-15*c*, and/or in conjunction with other wearable attachment devices, can contain various image processing, storage, and wireless communication capabilities and can be powered independently by rechargeable batteries, as already explained above.

FIG. 15*d* illustrates a wearable attachment device 1500*b* that is different than the wearable attachment devices of FIGS. 15*a*-15*c*. Rather than being attached to the arm or wrist of the user, the wearable attachment device 1500*b* is worn from the neck of the user by an adjustable strap 1510. The back of the user's neck is represented by reference line 1503 in FIG. 15*d*. As shown, the wearable attachment device 1500*b* is equipped with a folding and tilt mechanism 1512 coupled to the portable control and display unit 610. As such, the portable control and display unit 610 can be worn like a necklace close to the body of the user when not in use, and then unfolded for use where the user can easily view it.

Figure 15E:
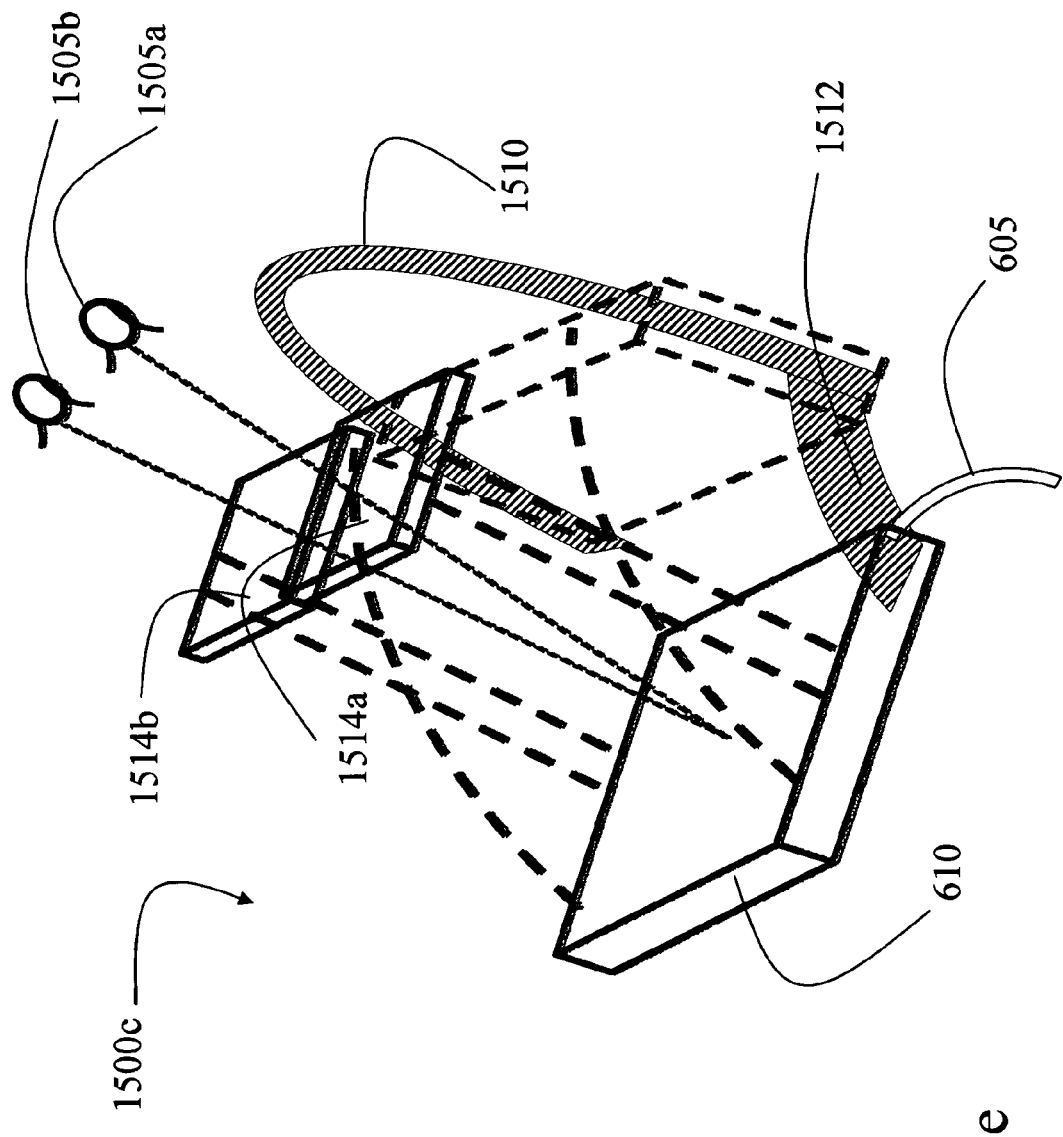
FIG. 15e illustrates the neck wearable, portable display of FIG. 15d that is further equipped with stereo viewing LCD shutter ports.

In another embodiment illustrated in FIG. 15*e*, a wearable attachment device 1500*c* is provided that is similar in some respects to the wearable attachment device 1500*b* of FIG. 15*d*. In particular, the wearable attachment device 1500*c* includes an adjustable strap 1510 and a folding and tilt mechanism 1512. In addition, the wearable attachment device 1500*c* includes a pair of time-synchronized LCD shutters 1514*a*, 1514*b*. The LCD shutters 1514*a*, 1514*b* act as input ports to viewing and are brought into position along the user's line of sight once the portable control and display unit 610 is unfolded or deployed in operating position. The left LCD shutter 1514*a* allows the left eye 1505*a* of the user to see the entire display only through the left LCD shutter 1514*a*, while the right eye 1505*b* of the user sees the full display only through the right LCD shutter 1514*b*, similar to 3D shutter glasses.

Wearable configurations, such as the wearable configurations of FIG. 15*e* where the user wears time-synchronized 3D shutter glasses or views the portable control and display unit 610 through independent LCD shutters positioned in front of the portable control and display unit 610, can be used for general stereoscopic viewing of imaging data stored or captured from a live imaging device, such as a stereo microscope, 3D x-ray or 3D fluoroscopic imaging data, etc. remotely.

To further secure the position and/or orientation of the portable control and display units 610 and/or wearable attachment devices depicted in FIGS. 15*a*-15*e*, optionally, although not shown, one or more straps, locking mechanisms and/or secondary clip attachment units can be used to fix the position and/or orientation of the portable control and display unit 610 with respect to the user's body during use. For example, in the arm-mounted wearable attachment devices of FIGS. 15*a*-15*c*, to prevent rotational movement of the portable control and display unit 610 around the arm, a Velcro or other strap could additionally secure the wearable unit around the user's thumb. Alternately or additionally, the neck-hanging wearable attachment devices 1500*b*, 1500*c* of FIGS. 15*d* and 15*e* can have a secondary strap around the user's body or a clip mechanism to the user's clothing, to prevent swinging or sideways motion of the portable control and display unit 610 as the user moves.

Figure 16:
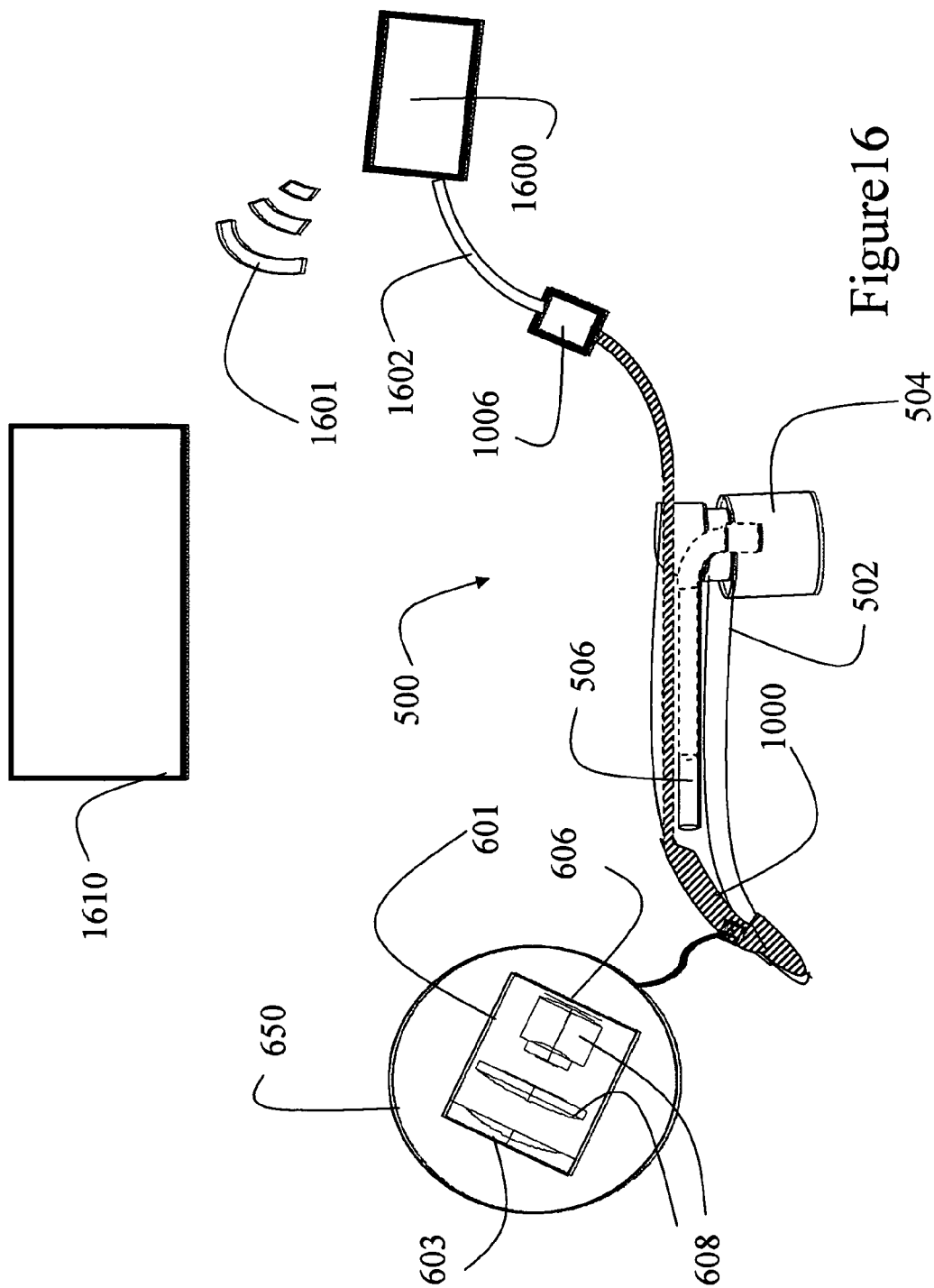
FIG. 16 illustrates a configuration that includes the wireless connection of the video laryngoscope of FIG. 10 to a remote display using a battery operated electronic control dongle connected to the OE vision module.

FIG. 16 illustrates a battery operated electronic control and transmission unit 1600 connected to the laryngoscope pluggable vision system 1000 of FIG. 10 as an electronic dongle. The electronic control and transmission unit 1600 powers the OE vision module 650 (see inset) in the attachable device 1000, processes imaging data from image sensor 606 of OE vision module 650, possibly compressing it, and transfers it wirelessly (represented by 1601) to a control and display unit 1610 with wireless capabilities. In some embodiments, the electronic dongle 1600 includes illumination and imaging control electronics and/or image processing electronics and a battery electrically connected to the electronics to power the electronics.

The wireless control and display unit 1610 can be similar in some respects to the portable control and display unit 610 described above. For instance, the wireless control and display unit 1610 of FIG. 16 can be portable and can generally include a display screen, a housing, and/or a power supply. Alternately or additionally, the wireless control and display unit 1610 can include illumination and imaging control electronics and/or image processing electronics. In contrast to the portable control and display unit 610, however, the wireless control and display unit 1610 of FIG. 16 is configured to communicate wirelessly with the OE vision module 650 and/or a corresponding OE illumination module.

The wireless control and display unit 1610 can be a display or control unit that is accessed by the electronic dongle 1600 via direct wireless broadcast, through a wireless network, or in cellular transmission. As such, each of the wireless control and display unit 1610 and electronic dongle 1600 can include a wireless transmitter (not shown) and/or receiver (not shown) to enable wireless communication between the control and display unit 1610 and electronic dongle 1600. The wireless transmitter and/or receiver of the wireless control and display unit 1610 serve as an example of a means for communicatively coupling the wireless control and display unit 1610 to the OE vision module 650 and/or to an OE illumination module via electronic dongle 1600 to communicate power and control signals and/or imaging signals between the wireless control and display unit 1610, the OE vision module 650 and/or an OE illumination module when the illumination and imaging control electronics and image processing electronics are included in the wireless control and display unit 1610. Alternately or additionally, the wireless transmitter and/or receiver of the electronic dongle 1600 serve as an example of a means for communicatively coupling the electronic dongle 1600 to one or more wireless control and display units 1610 to communicate power and control signals and/or imaging signals between the electronic dongle 1600 and the wireless control and display unit 1610 when part or all of the illumination and imaging control electronics and image processing electronics are included in the electronic dongle 1600.

Alternately or additionally, when the imaging control electronics and image processing electronics are included in the electronic dongle 1600, a cable 1602 comprising flex circuitry can communicatively couple the electronic dongle 1600 to the OE vision module 650 and/or to an OE illumination module. As such, the cable 1602 serves as an example of a means for communicatively coupling the electronic dongle 1600 to the OE vision module 650 and/or to an OE illumination module to communicate power and control signals and/or imaging signals between the electronic dongle 1600, the OE vision module 650 and/or and OE illumination module.

The electronic dongle 1600 can optionally include a local display screen for local viewing of images. Alternately or additionally, various mounting attachments similar or different from those illustrated in FIGS. 14*a*-15*e* can be provided for the electronic dongle 1600 and/or the wireless control and display unit 1610, with additional belt, or clip on mounting mechanisms for ease, convenience and safety in use of the electronic dongle 1600 and/or the wireless control and display unit 1610.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device for insertion into a body cavity, the device comprising:
    a hollow tubular device body having a proximal end and a distal end and a passageway extending therebetween, the distal end including a flexible and expandable portion configured to be inserted into the body cavity in an insertion position wherein the passageway of the hollow tubular device body is substantially closed at the distal end, the flexible and expandable portion further configured to be expanded radially outward to open the passageway of the hollow tubular device body at the distal end after being inserted into the body cavity;
    an opto-electronic illumination module including an illumination generating device positioned on a first side of the flexible and expandable portion of the distal end of the hollow tubular device body;
    an opto-electronic vision module including a camera housing, at least one camera lens, and a digital sensor positioned on a second side of the flexible and expandable portion of the distal end of the hollow tubular device body, the opto-electronic vision module being positioned substantially across from the opto-electronic illumination module after the flexible and expandable portion of the hollow tubular device body is expanded radially outward;
    a power source, control electronics, and a display device electrically coupled to the digital sensor of the opto-electronic vision module via electrical lines extending from the proximal end of the hollow tubular device body along a length of the hollow tubular device body to the distal end embedded from the proximal end to the distal end within a protective cover or jacket of the hollow tubular device body; and
    an electrical connector disposed at the proximal end of the hollow tubular device body, the electrical connector configured to electrically connect the power source, digital control electronics, and display device to the electrical lines;
    wherein the passageway enables access to the body cavity between the opto-electronic illumination module and the opto-electronic vision module.

2. The device of claim 1, wherein the opto-electronic vision module includes one or more of: a light emitting device (LED), a laser diode (LD), an ultraviolet (UV) light source, an infrared (IR) light source, a CCD sensor, and a CMOS digital sensor.

3. The device of claim 1, wherein the hollow tubular device body with embedded electrical line within the protective cover or jacket is one or more of: rigid, partially rigid, flexible and partially flexible.

4. The device of claim 1, wherein the device comprises any one of: a cannula, a speculum, or a catheter with a tool access hole inside the device.

5. The device of claim 1, wherein the hollow tubular device body is configured to be attached to: a direct laryngoscope blade or a medical access device devised to enter the hollow tubular device body through an incision or a natural orifice.

6. The device of claim 1, wherein the hollow tubular device body comprises a flexible tubular portion and wherein any one of a rigid, flexible, articulating or robotic medical body can be inserted through the flexible tubular portion of the device or otherwise attached to the device.

7. The device of claim 1, wherein the opto-electronic vision module and the hollow tubular device body are configured to be removably attached to a medical access device.

8. The device of claim 1, wherein the opto-electronic vision module is contained within a fully sealed and dry air filled housing within the hollow tubular device body, behind an airtight optical window.

9. The device of claim 8, wherein the fully sealed and dry air filled housing containing the opto-electronic vision module includes one or more moisture absorbing elements to maintain the air dry.

10. The device of claim 1, wherein the opto-electronic vision module comprises an digital image sensor, the device further comprising an imaging window interposed between the distal end of the hollow tubular device body and the digital image sensor, wherein heat from the digital image sensor or from a heat-generating resistor included in the device is coupled to the imaging window to substantially prevent formation of condensation on the imaging window.

11. The device of claim 1, wherein the opto-electronic illumination module includes an array of LED illuminators positioned on a first side of the distal end and an image sensor positioned on a second side of the distal end opposite the first side is such that in an insertion position, the opto-electronic vision module is substantially contained within a profile of the hollow tubular device body, and in a deployed position, at least a portion of the opto-electronic vision module is disposed external to the profile of the hollow tubular device body.

12. The device of claim 1, wherein the electrical connector is on an extended portion of the device with flexible cable.

13. A device for insertion into a body cavity, the device comprising:
a device body having a longitudinally extending wall defining a passageway extending between openings at each of a first end and a second, opposite end, the first end configured for insertion into the body cavity, wherein the first end is flexibly deployable from an insertion position in which the opening at the first end is substantially closed to a deployed position in which the opening at the first end is substantially open to accommodate insertion of a surgical tool through the passageway and into the body cavity;
a light source disposed at the first end of the device body on a first side of the device body;
a digital image capture device disposed at the first end of the device body on a second side of the device body, the digital image capture device being substantially across from the light source after the opening is in the deployed position; and
electrical circuitry electrically coupled to the light source and the digital image capture device and extending along a length of space in the device body within a protective cover or jacket of the device from the first end to the second, opposite end;
wherein the passageway enables access to the body cavity between the light source and the digital image capture device.

14. The device of claim 13, wherein the light source includes an array of light emitting diodes or laser diodes.

15. The device of claim 13, wherein the light source is configured to emit at least one of monochromatic light, polychromatic visible light, ultra violet light, and infrared light.

16. The device of claim 13, further comprising at least one of a highly conductive material and micro heat pipes disposed in the space within the device body and extending from the light source to the opening in the second, opposite end of the device body to transfer heat from light source through the wall of the device.

17. The device of claim 13, wherein the digital image capture device includes an opto-electronic vision module having at least one imaging lens and a digital image sensor disposed within a camera housing.

18. The device of claim 13, wherein the digital image capture device and the electrical circuitry coupled thereto are covered by and sealed within a protective cover.

19. The device of claim 17, wherein the light source and the digital image sensor are positioned such that the opening at the first end is at least partially unobstructed when in the deployed position.

20. A device for insertion into a body cavity, the device comprising:
a flexible device body including a channel extending between openings at opposite ends, a first end of the device body configured for insertion into the body cavity, the first end including a flexibly deployable portion configured to flexibly move between an insertion position and a deployed position, the flexibly deployable portion configured to be positioned over the opening to the channel such that the channel is substantially closed in the insertion position and configured to be deployed radially outward away from the opening to the channel such that the channel is substantially open to accommodate passage of a surgical tool through the channel and into the body cavity in the deployed position;
a digital camera unit disposed adjacent to the first end of the device body, at least partially within the channel, the digital camera unit being positioned on a side of the device body;
a plurality of light sources disposed adjacent the first end of the device body and spaced substantially across from the digital camera unit such that at least a portion of the openings at opposite ends are exposed to provide access to a void within the channel when the flexibly deployable portion is in the deployed position; and
electrical lines electrically coupled to the digital camera unit and the plurality of light sources housed from the first end of the flexible device body to a second end within a protective cover or flexible jacket of the device body.

21. The device of claim 20, wherein the electrical lines extend along a length of the channel, and terminate at an electrical connector disposed adjacent a second end of the device body opposite the first end.

22. The device of claim 20, wherein the plurality of light sources includes at least two light emitting diodes of various wavelengths positioned on opposite sides of the digital camera unit.

23. The device of claim 20, wherein the plurality of light sources includes at least one color synchronized black and white digital image capture device to provide digital spectral images.

24. The device of claim 20, further comprising an articulating or deployment mechanism inside the channel of the device body, the articulating or deployment mechanism attached to at least one of the plurality of light sources or vision module and configured for moving the at least one of the plurality of light sources or vision module from a first position to a second position.

25. The device of claim 20, wherein the device body includes an endoscope, a cannula, or a speculum.

* * * * *